(12) United States Patent
Chammas

(10) Patent No.: US 8,876,683 B2
(45) Date of Patent: Nov. 4, 2014

(54) AUTOMATED SYSTEM AND METHOD FOR BLOOD COMPONENTS SEPARATION AND PROCESSING

(76) Inventor: Jacques Chammas, Walpole, MA (US)

( * ) Notice: Subject to any disclaimer, the term of this patent is extended or adjusted under 35 U.S.C. 154(b) by 1134 days.

(21) Appl. No.: 12/139,614

(22) Filed: Jun. 16, 2008

(65) Prior Publication Data
US 2008/0248938 A1    Oct. 9, 2008

Related U.S. Application Data

(63) Continuation of application No. 11/076,130, filed on Mar. 9, 2005, now Pat. No. 7,442,178.

(51) Int. Cl.
*B04B 15/00* (2006.01)
*B04B 13/00* (2006.01)

(52) U.S. Cl.
USPC .............. 494/10; 494/84; 422/533

(58) Field of Classification Search
USPC .............. 494/10, 18, 84; 210/782, 787; 604/4.01–6.16; 422/533
See application file for complete search history.

(56) References Cited

U.S. PATENT DOCUMENTS

| | | |
|---|---|---|
| 3,211,368 A | 10/1965 | Shanley |
| 3,674,197 A | 7/1972 | Mitchell et al. |
| 3,987,961 A | 10/1976 | Sinn et al. |
| 4,135,883 A | 1/1979 | McNeil et al. |
| 4,187,979 A | 2/1980 | Cullis et al. |
| 4,227,814 A | 10/1980 | Soodak et al. |
| 4,316,576 A | 2/1982 | Cullis et al. |
| 4,322,298 A | 3/1982 | Persidsky |
| 4,413,771 A | 11/1983 | Rohde et al. |
| 4,447,220 A | 5/1984 | Eberle |
| 4,608,178 A | 8/1986 | Johansson et al. |
| 4,720,284 A | 1/1988 | McCarty |
| 4,810,090 A | 3/1989 | Boucher et al. |
| 4,915,847 A | 4/1990 | Dillon et al. |
| 4,946,434 A | 8/1990 | Plaisted et al. |
| 5,102,407 A | 4/1992 | Carmen et al. |
| 5,330,462 A | 7/1994 | Nakamura |
| 5,405,308 A | 4/1995 | Headley et al. |
| 5,674,173 A | 10/1997 | Halvinka et al. |
| 5,707,331 A | 1/1998 | Wells et al. |
| 5,723,050 A | 3/1998 | Unger et al. |
| 5,769,839 A | 6/1998 | Carmen et al. |
| 5,770,069 A | 6/1998 | Meryman |
| 5,792,038 A | 8/1998 | Halvinka |
| 5,836,934 A | 11/1998 | Beshel |
| 5,921,950 A | 7/1999 | Toavs et al. |
| 6,019,716 A | 2/2000 | Forestell et al. |

(Continued)

FOREIGN PATENT DOCUMENTS

WO    WO95/01842    1/1995

OTHER PUBLICATIONS

Wilson et al., "The NEES Geotechnical Centrifuge at UC Davis." Aug. 2004.*

*Primary Examiner* — Timothy Cleveland
(74) *Attorney, Agent, or Firm* — Novak Druce Connolly Bove + Quigg LLP

(57) ABSTRACT

A blood processing centrifuge comprising: a rotor having an axis of rotation and being controllably spun around the axis, a mechanism for processing whole blood within the rotor while spinning, a computer controlling blood processing operations, the computer being mounted to the rotor and spinning therewith.

20 Claims, 17 Drawing Sheets

(56) References Cited

U.S. PATENT DOCUMENTS

| | | |
|---|---|---|
| 6,123,655 A | 9/2000 | Fell |
| 6,132,354 A | 10/2000 | Ohtsu et al. |
| 6,143,183 A * | 11/2000 | Wardwell et al. ............... 494/10 |
| 6,251,284 B1 | 6/2001 | Bischof et al. |
| 6,261,217 B1 | 7/2001 | Unger et al. |
| 6,315,706 B1 | 11/2001 | Unger et al. |
| 6,322,709 B1 | 11/2001 | Krasnoff et al. |
| 6,325,750 B1 | 12/2001 | Jorgensen et al. |
| 6,348,031 B1 | 2/2002 | Unger et al. |
| 6,495,039 B1 | 12/2002 | Lee et al. |
| 6,605,223 B2 | 8/2003 | Jorgensen et al. |
| 6,652,475 B1 | 11/2003 | Sahines et al. |
| 2001/0034513 A1 | 10/2001 | Rubinstein |
| 2003/0191005 A1 | 10/2003 | Coelho |
| 2004/0140012 A1 | 7/2004 | Sommer |
| 2004/0254560 A1 | 12/2004 | Coelho |

* cited by examiner

AUTOMATED SYSTEM AND METHOD FOR BLOOD COMPONENTS SEPARATION AND PROCESSING

RELATED APPLICATIONS

This application is a continuation of and claims the benefit of priority of U.S. application Ser. No. 11/076,130, filed Mar. 9, 2005 the disclosure of which is incorporated herein by reference in its entirety as if fully set forth herein.

FIELD OF THE INVENTION

The present invention relates to apparati and methods for processing of blood and more particularly to automated systems and methods for separating components of blood into discrete fractions.

BACKGROUND OF THE INVENTION

Transfusion therapy in the past was largely dependent on the use of whole blood. While whole blood may still be used in certain limited circumstances, modern transfusion therapy depends largely on the use of clinically needed blood component. Whole blood consists of many components, primarily, red blood cells, white blood cells, platelets, and plasma. Therefore, a whole blood unit that is collected from a normal donor can be processed to separate it into its components. Each component can then be transfused to a needy individual.

Centrifugation is a known technique for separating blood into its individual components. This is possible because each blood component has its own density. Therefore when whole blood is subjected to high centrifugal force, the components of different densities are separated. When a whole blood container is placed in a rotating centrifuge, red blood cells (RBC) of the highest density are concentrated in a section of the container that is the most distant from the axis of rotation of the container. White blood cells (WBC) having the second highest density are concentrated in a layer supported by the RBC layer and are positioned closer to the axis of rotation. Platelets with a density slightly less than that of the WBC are clustered in a layer adjoining the WBC layer closer to the axis of rotation. Plasma with the least density is packed in a layer the closest to the axis of rotation.

At high centrifugation speed (hard spin), the blood is separated into three layers, an RBC layer, a mixture of WBC and platelets called "Buffy Coat" layer, and a plasma layer. At low centrifugation speed (soft spin), blood is separated into two layers, RBC and platelets rich plasma (PRP). A sharp and distinct edge is formed at the boundary of the separated RBC layer and PRP layer. These sharp edges are maintained by constant rotation of the centrifuge, and rapidly disintegrate when the centrifuge stops rotating.

Current blood separation techniques that are widely used in blood banks start by spinning a whole blood containing bag at a low speed in a large centrifuge. Distinctive RBC and PRP layers are formed in the blood (primary) bag. The centrifuge is then stopped and the primary bag is carefully removed from the centrifuge and placed in an extractor. The difficulty in this step is not to disturb the separation edge between the two layers. The PRP is manually squeezed out of the bag into an empty satellite bag connected to the primary bag. The RBC remaining in the primary bag is mixed with additive solution to preserve the RBC for storage. In most applications the RBC and additive solution mixture is directed through a leukocyte reduction filter to remove the white blood cells (WBC) from the RBC concentrate.

The satellite or auxiliary bag containing the PRP is then placed in the centrifuge and spun at a higher speed until the platelets are sedimented and a concentrated platelet layer and platelets poor plasma (PPP) layer are formed. The bag is carefully removed from the centrifuge without disturbing the separation edge and placed in a manual extractor. The PPP is expressed into a second satellite or auxiliary bag connected to the first satellite bag, leaving a platelet concentrate in the first satellite bag.

This current technique is labor intensive where human factor has imperative effect on product quality and purity. Contamination (unwanted RBC or WBC mixed with plasma or platelets) is a known threat to product quality. Among the reasons that cause platelets rich plasma contamination are the tendency of the top portion of the blood bag to fold during centrifugation and entrapping RBC. Following centrifugation, the entrapped blood cells can be released into the previously separated platelet-rich plasma. Another source of contamination of the PRP is the tendency of the bags contents to swirl during rotor deceleration in an effort to preserve its angular momentum causing RBC and WBC to be mixed with plasma.

Furthermore the handling of the blood bag after centrifugation and the way it is placed it in the extractor may cause contamination of the plasma by RBC or WBC.

More recently, automated extractors have been introduced in order to facilitate the manipulation of whole blood units. Nevertheless, the whole process remains laborious and requires the transfer of separated components from the primary bag to a satellite bag, to be completed quickly with manual intervention before disintegration of the separation edge in order to maintain product purity.

Moreover, the overall blood separation process has to be completed and the separated components have to be used or stored under appropriate conditions within a certain period of time after the blood collection to guarantee the quality and the medical integrity of the blood components. This time limit requires all blood processing procedures to be conducted efficiently and effectively in an environment heavily dependent on human factor and manual operations.

There have been many attempts to automate blood processing and transferring separated components from one bag to another while the centrifuge is rotating.

U.S. Pat. No. 4,447,220 discloses one method of placing a blood bag in a centrifuge rotor to separate RBC or plasma, and then displace RBC or plasma to a connected satellite bag by squeezing blood bag using a pressure pad, or by centrifugal force while the centrifuge is spinning.

U.S. Pat. No. 6,261,217 discloses a method of separating whole blood into RBC, plasma, and buffy coat by spinning a flexible disk.

U.S. Pat. No. 5,770,069 discloses a method and apparatus for separating blood components and washing or glycerolizing RBC by spinning multiple bags U.S. Pat. No. 3,211,368 discloses a method and apparatus for blood separation and treatment of separated components including RBC washing and Glycerolization.

U.S. Pat. No. 6,605,223 discloses a method and apparatus for separating several units of blood into components by spinning cassettes containing multiple bags.

SUMMARY OF THE INVENTION

The present invention provides a new automated method and apparatus for separating and treating blood components (plasma, platelets, white blood cell "WBC", red blood cell "RBC", etc) by centrifuging blood fluid in the rotor of a centrifuge, where the blood fluid is contained in a primary bag that is interconnected to a number of satellite bags and set in the rotor, whereby the separation of the components of different densities is achieved by centrifugation, followed by the segregation of each component in a separate bag, mix the components that require further treatment with therapeutic solution, then express the excess solution from the treated component bag, while the rotor is spinning.

The invention provides an automated method and system for simultaneously separating multiple blood units into their components. The automated process reduces cost by eliminating laborious laboratory steps that are inherent in the current separation methods. The automated process improves the quality of the product by minimizing human factors and maintaining process consistency and efficiency. Product quality and purity are enormously enhanced by segregating blood components while the centrifuge is spinning and preserving the separation edge between the different layers. Blood components, red blood cell (RBC), plasma, Platelets, and Leukocytes known as white blood cell (WBC) are segregated in separate bags.

Preferably the method and system according to the invention proceed automatically to mix blood components that require treatments by a therapeutic solution, then extract out the excess solution. These therapeutic treatments include but are not limited to mixing concentrated RBC with additive solution to preserve it for up to 42 days storage, glycerolize concentrated RBC to preserve it for up to 10 years, mixing concentrated RBC with Glucose for storage, washing RBC, washing Platelets, and mixing RBC with rejuvenating solution.

Segregating the leukocytes from the other components has many benefits in the modern medicine. Most importantly, the reduction of the WBC count in the RBC, Plasma, and platelets improve their medical quality. Also segregated WBC layer helps in isolating stem cells that are widely used for biotech therapeutic applications. Companies are currently isolating stem cells from umbilical cord blood to be stored at very low temperature for future use.

The disposable set of containers disclosed in this application typically comprises a primary bag interconnected for fluid flow to four satellite bags. One satellite bag contains a therapeutic solution and/or preservative solution. All bags are preferably comprised of flexible plastic films. The primary bag and at least one satellite (plasma) bag has a main chamber having a coned shaped top end with tapered sides connected to a small atrium, i.e. a small defined portion of the volume of the bag that is disposed immediately in communication with the exit of the bag/container having the shape of a convergent funnel leading to the exit port or aperture at the top end of the bag. The geometry of the exit end (the proximal end) of the bag/container is most preferably configured as a cone-like shaped portion that merges into a narrower atrium portion. This geometry at the exit end of the bag/container helps in evenly streamlining the exiting fluid flow through the exit port while the centrifuge is still spinning and assists in preserving the separation edge between the exiting fluid and the remaining fluid as it converges in its flow through the exit port of the bag/container. Tubes interconnecting primary and satellite bags are typically equipped with at least two manifolds containing flow intersection points. These manifolds further assist in mounting the disposable set of containers within the centrifuge apparatus in stable and correct positioning, interconnection and engagement, particularly with respect to flow control valves and sensors. Most preferably, a connecting tube is provided that interconnects the primary bag and a phlebotomy needle that is used to deliver blood from a donor and collect it in the primary bag.

A centrifuge apparatus according to the invention has an array of cradles spaced evenly around the axis of a centrifuge rotor. Each cradle is typically hinged to a load cell that is rigidly interconnected to the rotor.

The rotor comprises a cylindrical shaped drum at its center mounted above a rotating spindle with all entities, rotor, drum, and spindle having the same axis of rotation. As used herein the word "Computer" means but is not restricted to all types of computers and microcomputers built with any type of discrete or integrated microprocessor, or any type of discrete or integrated microcontroller. Such microprocessors or microcontrollers may or may not include other components such as memory (RAM, ROM, PROM), memory management, caches, floating-point unit, input/output ports and timers. The definition of word "Computer" also includes any assembly or grouping of discrete or integrated transistors utilized in any computing or decision making process. An upper portion of the drum preferably contains all necessary electronic circuit boards, chipsets, computers and the like that are used/programmed to operate and control the timing/sequence, duration, load, speed, intensity and the like of one or more or all of any valves, sensors, load cells, photocells, switches, motors, pumps, solenoids, and wireless communication devices that are included with and that spin with the rotor of the centrifuge system. The spinning electronic circuit boards or computer typically contain a computer that controls, communicates with, instructs, and receives feedback from all electrical, electronics and pneumatic devices and systems located on the spinning rotor. The electronic circuit boards preferably control the rotor and its speed. The spinning electronic circuit boards/computer is most preferably interconnected with remotely located electronic/electric devices and computers that are remotely disposed and do not spin with the rotor of the centrifuge. The spinning computer includes memory to store and exchange data, instructions, commands and information generally. The spinning computer preferably includes executable programs and a processor to carry out these programs. The system most preferably includes a mechanism that enables the spinning computer to directly communicate with the remote, non-spinning stand alone devices and computers. Such mechanisms preferably comprise a data cable interconnected between the spinning computer and the remote devices via a family of slip rings or wireless communication channels to transfer data back and forth between the rotating computer and the remote stationary or stand alone devices.

Electric power is typically supplied to all electrical and electronic devices on the spinning rotor by an electrical conduit that extends through a passage in the spindle to a conventional slip ring at the base of the spindle. The power source is typically connected to the slip ring by means of a brush contact. Another slip ring on the spindle is connected to ground by a brush contact.

The lower section of the drum of the centrifuge typically contains an annular shaped reservoir on the periphery filled with high density fluid. An array of evenly spaced pumps (equal to the number of cradles) preferably pump a selected amount of high-density fluid from the annular reservoir to a ballast located on the cradle so as to centrifugally balance each cradle. A selected amount of high-density fluid is automatically added to the ballast to dynamically balance the rotor by equating the weight of each cradle. The central portion of the lower section of the drum typically contains a pressurized air tank. The compressed air is used to activate pneumatic valves and actuators on the rotor. The pressurized air is supplied to the tank by a compressor located on a stationary structure of the centrifuge and is fed to a rotating seal at the bottom of the spindle. An air passageway is located at the center of the spindle of the centrifuge and extends vertically through the spindle from a rotary seal at the bottom upwardly to the air tank.

The disposable set of bags is most preferably installed in a chuck before the set of processing/collecting bags are mounted to the centrifuge rotor. A "chuck" according to the invention is a portable component readily mountable in and dismountable from the centrifuge to facilitate installation of the set of blood processing/collection bags or containers. The chuck is preferably lightweight and readily loadable by hand with a set of bags/containers. The primary bag or container that contains the original whole blood fluid to be separated into its components is typically inserted in a support pouch. The two or more fluid flow manifolds are snap fitted into their appropriate locations and the satellite bags are disposed in their apposite chambers inside the chuck. A chuck carrying loaded with a set of bags/containers is docked in the cradle of the centrifuge. The cradle as shown in the accompanying figures typically has the shape of a rectangular box configured to receive a chuck that is configured to a complementary shape. As shown herein, each cradle has two sets of pneumatic valves located at the two radial extremities of the cradle and are prepared to be engaged with the manifolds from the blood processing set. An optic sensor that detects fluid characteristics such as density is located at the front end of the cradle near the rotating axis. A deformable pressure pad that inflates by pressurized air is disposed between the two valve sets. When the chuck is coupled to/mounted in the cradle, the primary blood bag/container that is inserted in the support pouch and a pressure pad provided for squeezing the bag are confined within a fixed space. The volume of the expandable pressure exerting pad increases only when the volume of the primary blood bag decreases.

The invention provides for automatic engagement of all of the individual bags/containers of a full processing set of bags with each of their corresponding fluid flow control valves, actuators, and sensors included in the system when the chuck is first mounted/nested in the cradle. The chuck is automatically physically secured to the cradle against disengagement from spinning force or other movement upon nesting/mounting.

Another aspect of the invention provides for an automated method of blood separation and treatment of the components of whole blood. A computer program stored in the rotor embedded computer or in the stationary computer instructs all modules on the rotor to execute a series of predetermined steps in a precise predetermined order. Each program that accomplishes certain objective is defined as a protocol. For example one protocol can be just separating blood and segregating components. Another protocol can be separating blood, segregating components and mixing RBC with additive solution.

The rotor embedded computer includes instructions, processors, memory and programs for evaluating all feedbacks it receives from all modules and sensors, for responding to all commands, and for directing the execution of all programs accordingly.

After loading all the cradles in the centrifuge rotor with chucks fitted with all sets of blood processing bags, the operator inputs the desired protocol to command the desired process to start. The computer takes charge of completing the whole process automatically. In a preferred embodiment, the centrifuge rotor rotates at a certain speed for the rotor to dynamically self balance itself before increasing its rotational speed to achieve an initial RBC and platelet rich plasma separation. The rotor spins for a predetermined amount of time, e.g. about 3 minutes, at a relatively low speed known as "soft spin" separating the blood in the primary bag to RBC layer and platelets rich plasma (PRP) layer forming a distinctive edge at the boundary of the two layers. Since RBC have higher density, they are disposed in the radially outward or distal portion of the primary bag. The PRP are closer or more proximal to the axis of rotation. The valves controlling the flow between the primary bag and the plasma bag (i.e. RBC valve and plasma valve) are opened. At the same time a pressure pad for squeezing the primary bag is expanded with pressurized air and starts to squeeze the primary bag forcing the less dense PRP disposed at the exit end of the bag to be transferred through the exit through a connecting tube to an empty auxiliary plasma bag. As the fluid exits the primary bag it passes through an optic sensor that monitors the density of the fluid and communicates information to the computer. The pressure pad continues to squeeze the PRP out of the primary bag until the optic sensor detects a change in fluid density. On detection of a change in fluid density (or other predetermined fluid property) the valves are closed and the PRP flow to the plasma bag is stopped. The pressure in the pressure pad is partially relieved, allowing the RBC inside the primary bag to move distally away from the exit port of the bag under the constant centrifugal force. Most preferably, the rotor is slowed down when the PRP has been transferred to the auxiliary bag. The pressure pad is preferably expanded by pneumatic or hydraulic slowly causing it to gently squeeze the primary bag and force the PRP out of the exit port without disturbing the separation edge between the PRP and RBC layers that are formed inside the primary bag under the soft spin phase of the cycle.

With PRP in the plasma bag and RBC in the primary bag, the rotor is next spun at higher speed "hard spin" for a predetermined amount of time, e.g. for about 7 minutes. During the hard spin phase, the blood plasma and the platelets are separated in the plasma bag. The higher density platelets are disposed in a more radially outward section of the plasma bag, and the pure plasma is disposed closer to the axis of rotation. The exit port of the plasma bag in this instance is located on a radially distal periphery of the bag. A bag for receiving platelets is disposed in a radially distal compartment location relative to the plasma bag. Since the platelets are located at the radially distal portion, the exit port of the plasma bag is also positioned at a radially distal location and is preferably formed in a funnel configuration. Upon separation of the platelets from the plasma, a valve is opened that allows flow between the plasma bag and the platelet bag (i.e. platelets valve). When the platelets valve is open, the platelets rush out of the plasma bag under the centrifugal force of the spinning rotor and the platelets are deposited in the platelets bag. The platelets valve is opened for a predetermined period of time long enough to allow all platelets and about 50 ml of plasma to be delivered to the platelets bag. It is preferable to open and close the platelets valve intermittently until all platelets exit the plasma bag in small bursts of platelets concentrate. For example the platelets valve is opened for one second allowing a burst of platelets to exit the plasma bag, and then the valve is closed for 10 seconds permitting the platelets layer to be re-packed and the separation edge to be sharpened again under centrifugal force. The valve is then opened again for one second, and so on until all platelets and 50 ml of plasma exit the plasma bag.

During the hard spin phase, in the primary bag, the RBC and the buffy coat (mostly leukocytes) are separated, and a small layer of plasma is formed in the exit port area closest to the axis of rotation. The pressure pad is inflated to gently squeeze the plasma out of the primary bag, and the RBC and the plasma valves are then opened. When the optic sensor detects a change in the exiting fluid density, the RBC and plasma valves are closed and the valve controlling the flow between the primary bag and the WBC bag (i.e. Leukocytes valve) is opened for a period of time long enough to allow for the buffy coat to be transferred to the WBC bag.

It is preferable to open and close the leukocyte valve intermittently until the entire buffy coat exits the primary bag in small bursts of leukocytes concentrate. For example the leukocytes valve opens for one second allowing a burst of buffy coat to exit the primary bag, and then the valve closes for 15 seconds permitting the buffy coat layer to be re-packed and the separation edge to be sharp again. The valve opens for one second again, and so on until the entire buffy coat exits the primary bag.

After the hard spin and separation phases described above, the centrifuge rotor is next spun at low speed with the RBC being disposed in the primary bag, the leukocytes in the WBC bag, the plasma in the plasma bag, and the platelets in the platelets bag. The pressure pad is then partially deflated relieving the pressure on the RBC in the primary bag. The RBC are packed in the radially outermost section of the bag, the front end of the bag near the rotating axis is empty and has a negative pressure forcing the bag film to collapse.

A therapeutic treatment solution bag is oriented inside the chuck with its exit port pointing and disposed in a radially distal location. When the solution valve is opened, the solution rushes out of the solution bag under centrifugal force.

Depending on the selected protocol, the therapeutic solution is transferred to the component bag that needs treatment. For example if additive solution need to be mixed with RBC to preserve it for 42 days storage, solution valve and plasma valve that control the flow between the solution bag and the RBC bag are open. The solution is delivered out of the solution bag by centrifugal force and it is sucked in by the negative pressure inside the primary bag.

If the selected protocol requires the RBC to be mixed or washed by a therapeutic solution and then express the excess solution out of the primary bag that contains RBC, the above steps are repeated to enable the solution to mix with the RBC in the primary bag. The plasma valve is closed and the centrifuge starts to spin in alternate mode between high and low speed. The pressure pad inflates and deflates repeatedly to thoroughly mix the solution with the concentrated RBC. The alternating centrifuge speed and pressure squeeze continue for a period of time enough to ensure thorough mixing. The centrifuge starts spinning at high speed for about 2 minutes to separate the RBC from the solution inside the primary bag. The RBC having high density sediment at the radially outermost part of the bag and the solution layer is settled close to the axis of rotation near the exit port. Plasma valve and solution valves are opened and the pressure pad inflates to squeeze the excess solution out of the primary bag. The excess solution is displaced to the solution bag until the optic sensor detects a change in the density. At this point, plasma valve and solution valves are closed and the centrifuge stops.

In another alternative embodiment the platelets can be washed. In this embodiment, a second pressure pad is situated on the cradle in a way such that when the chuck is secured to the cradle, said pad and the platelets bag are curbed in a rigid space. At the end of the separation process, the solution valve and the platelets valve are open and the wash solution is delivered to the platelets bag. After mixing the platelets with the wash solution, the pressure pad squeeze the extra solution out of the platelets bag and force it in the solution bag.

In other embodiments moving plates activated by electric motors or pressurized air powered motors, can be used to squeeze the primary bag and platelets bag instead of a pressure pad. Solenoid activated valves can be used instead of a pneumatic or hydraulic valve. Ultrasound sensor detecting fluid density can also be used instead of optic sensors.

In another embodiment peristaltic pumps spinning with the rotor can be used to pump fluid in and out of the primary and the platelets bag.

In another embodiment the primary bag can be situated in the chuck with the exit port is oriented radially outward. After the centrifuge separates RBC and PRP in the primary bag, the RBC valve located at a position radially beyond the exit port, is opened. RBC are delivered out of the primary bag by centrifugal force and received in an empty WBC bag situated in a chamber above or below the primary bag. The RBC valve is closed when an optic sensor at the exit port of the primary bag detects PRP. The centrifuge spins at higher speed until platelets and plasma are separated in the primary bag and RBC and buffy coat are separated in the WBC bag. The higher density platelets are deposited in the radially distal portion of the primary bag near the exit port. In the WBC bag, the higher density RBC layer is sedimented in the radially distal portion of the bag.

The platelets valve opens for a period of time allowing the platelets to exit the primary bag and be delivered into a platelets bag disposed vertically in compartment positioned radially beyond the exit port. WBC valve controlling the flow between WBC bag and a satellite bag is opened allowing the RBC to exit the WBC bag by centrifugal force. RBC are delivered into a satellite bag placed vertically in a compartment located radially beyond the WBC valve. The WBC valve is closed when the optic sensor at the exit port detects buffy coat.

Any selected series of processing steps may be programmed into the computer/circuit boards that are embedded or attached to the rotor. The above described protocols/methods being typically preferred examples.

In accordance with the invention there is provided A blood processing centrifuge, comprising: a rotor having an axis of rotation, means for processing whole blood within the rotor, a computer controlling blood processing operations, the computer being mounted to the rotor and spinning therewith. The embedded computer or circuit boards 90 is/are typically mounted within less than about 24 inches from the axis of rotation, preferably less than about 0.5 inches.

The computer can be hard wire interconnected by data transmission wires to a second computer disposed in a location remote from the rotor, the rotor including one or more slip rings for enabling the hard wire interconnection. Alternatively the computer can includes a wireless data transfer mechanism, the computer sending data signals via the wireless data transfer mechanism to a second computer disposed in a location remote from the rotor. The second computer comprises one or more of portable computer, a stationary computer, a network of computers, a remote control device, a microprocessor, video display monitor or a digital memory device.

The rotor embedded computer preferably includes: one or more programs that include instructions for executing blood processing operations, a mechanism for sending and receiving one or more data or instruction signals to and from other digital data processing or storage devices comprising one or more sensors, monitors, gauges, drivers, motors, valves or actuators, wherein the other devices are mounted within the rotor, and, a wireless communication mechanism that effects communication of signals between the computer and one or more electronic devices disposed in a location remote from the rotor.

Further in accordance with the invention there is provided a biological fluid processing apparatus comprising: a primary container storing a biological fluid containing materials of different densities, a plurality of expandable auxiliary containers interconnected for fluid flow to and from the primary container by fluid sealed tubes, at least one of the auxiliary containers containing a fluid for treating the biological fluid.

In another aspect of the invention there is provided a centrifuge system for separating a biological fluid containing materials of different densities into its components, comprising: a rotor having an axis of rotation, a computer controlling biological fluid separation procedures, the computer being mounted in the rotor and spinning therewith, a chuck having a biological fluid separation apparatus mounted within the chuck, the fluid separation apparatus comprising a plurality of containers interconnected by fluid flow enabling tubes, one or more of the containers containing the biological fluid, a plurality of cradles connected to the rotor for co-rotation therewith around the axis, the chuck being securely mountable in a cradle for rotation around the axis, a mechanical or electromechanical apparatus enabling selective flow of fluid between selected ones of the containers, the operation of the mechanical apparatus being controlled by the computer.

The system preferably includes one or more sensors for sensing a distinguishing property of fluid at one or more locations within the separation apparatus wherein the sensors are connected to the computer for sending signals indicative of the distinguishing property of the fluid to the computer. The biological fluid is separated by centrifugal force within one or more of the containers into discrete layers of materials of different densities wherein the computer includes instructions for directing operation of the mechanical or electromechanical apparatus to separate the materials of different densities into separate containers while the system is being maintained under centrifugal force. The mechanical or electromechanical apparatus comprises one or more valves disposed between the containers, the valves being controllably operable by the computer under centrifugal force.

The mechanical or electromechanical apparatus can comprise a compressor that is controllably operable by the computer to controllably compress a container containing layers of materials of different densities such that one layer is compressed out of the container to another container under centrifugal force. The speed of the rotor is preferably controlled by the computer.

The mechanical or electromechanical apparatus can comprise one or more peristaltic pumps controlled by the computer to direct fluid flow from at least one container to another container inside said chuck.

Flow from one container to another container within a chuck can be carried out by centrifugal force.

The mechanical or electromechanical apparatus can comprise a controllably expandable body, at least one container being flexible and containing biological fluid and being mounted within a chamber of defined space within the chuck, the computer directing the expandable body to controllably expand against a wall surface of the at least one container to controllably squeeze fluid out of the at least one container while under centrifugal force.

The mechanical or electromechanical apparatus can comprises at least one rigid body controllably movable by the computer, at least one container being flexible and containing biological fluid and being mounted within a chamber of defined space within the chuck, the computer directing the rigid body to push against a wall surface of the at least one container to controllably squeeze fluid out of the at least one container. The rigid body is adapted to push by centrifugal force. The rigid body can push under the force of an electromechanical device selected from the group consisting of electrical motors, solenoids, and electromagnets. The rigid body can push under the force of a pneumatic device selected from the group consisting of turbo motors, inflatable bodies, and pistons.

The sensors are typically selected from the group consisting of photoelectric sensors, optic sensors, ultrasonic sensors and magnetic resonance imaging sensors.

The computer includes instructions for directing the flow of at least one biological fluid treating solution from one container to another container within said chuck.

The rotor preferably includes a dynamic self balancing mechanism that automatically configures the weight of each processing station and pumps a preselected amount of high-density fluid to a balancing ballast contained within each cradle to synchronize the weight of the stations.

In another aspect of the invention there is provided a disposable set of a plurality of blood collecting and processing containers mounted as a set in a centrifuge comprising a primary container to collect and store blood and a satellite container, the plurality of containers being linked by interconnecting tubing and one or more manifolds at least one satellite container containing blood product treatment solution.

The primary container comprises a main chamber having an atrium communicating with a first tube, the main chamber having edge-seals arranged generally parallel to a longitudinal axis of the container, the edge seals merging with first tapered edge-seals that lead to said atrium, the atrium being defined by second tapered edge-seals extending from the first tapered edge-seals. The primary container is formed by heat sealing two flexible thermoplastic films and has opposing edge-seals generally parallel to the longitudinal axis and merged with a set of tapered edge-seals leading to said first tube.

The first and second tapered edge-seals are disposed at an angle of between 10 degrees and 170 degrees the angle for the second tapered edge seal is about 120 degrees and the angle for the first edge seal about 70 degrees for said atrium. The atrium has a volume of between 1 ml and 100 ml and preferably about 10 ml.

The first tube typically lies on the longitudinal axis. A second tube can communicate with the interior of the chamber by extending to the bottom of the container.

The disposable set of containers can include a plurality of rigid or semi-rigid manifolds automatically interconnectable with valves, actuators or sensors to direct fluid flow among the set of containers.

Further in accordance with the invention there is provided a system for automatically separating blood into components and selectively treating the components with therapeutic solution inside a rotating centrifuge, the system comprising:

a rotor having an axle, a computer for controlling blood component separation, segregation and processing operations, the computer being embedded in or mounted to or on said rotor and spinning therewith, a chuck for securely mounting a plurality of interconnected blood containers to the rotor, the chuck being readily mountable to and dismountable from the rotor, a plurality of equally spaced cradles interconnected to the rotor in a common plane perpendicular to the axis of rotation of the rotor, the cradles including a seat for securely holding a chuck.

The portion of the fluid driven out of the container is one or the other of the less dense and more dense portions.

The fluid portion driven out of the container can be a portion having a density intermediate to the less dense and said more dense portions. The fluid portion driven out of the container can be transferred to an auxiliary container while the fluid is spinning. The selected portion of the fluid driven out of the container is driven out in a predetermined volume. A treatment solution is mixed with said more dense fluid portion while the fluid is spinning.

The invention also provides a method of automatically separating a biological fluid into portions of different densities and segregating each portion into a separate container inside a rotating centrifuge having an axis of rotation, comprising the steps of:

mounting a plurality of containers in the centrifuge, the containers including at least a primary container containing the biological fluid and at least a first auxiliary container interconnected to the primary container by a closed channel, at least a second auxiliary container interconnected to the first auxiliary container by a closed channel, spinning the plurality of containers around the axis of rotation at a selected rotational speed for a selected period of time until a distinct separation edge is formed between a more dense portion of the fluid positioned more distally relative to the axis and a less dense portion positioned more proximally relative to the axis of rotation, driving the less dense portion of fluid out of the primary container into the first auxiliary container, while the containers are being spun at a speed that maintains the distinct separation edge, sensing the density of the fluid being driven out of the primary container and stopping the driving out of the container upon sensing of a predetermined change in the density, spinning the plurality of containers around the axis of rotation of the centrifuge at a second selected higher rotational speed for a second selected period of time until the fluid in the first auxiliary container is separated into a more dense portion positioned more distally relative to the axis of rotation and the less dense portion is positioned more proximally relative to the axis of rotation with a clear separation edge being formed between the two portions in the first auxiliary container, the fluid in the primary container being separated into a more dense portion positioned more distally relative to the axis of rotation and the less dense portion being positioned more proximally relative to the axis of rotation with a clear separation edge being formed between the two portions in the primary container, driving one portion of fluid of a defined density out of the first auxiliary container and into a second auxiliary container while the centrifuge is turning at a speed that maintains a distinct separation edge between the separated portions, driving one portion of fluid of a defined density out of the primary container and into an auxiliary container while the centrifuge is turning at a speed that maintains a distinct separation edge between the separated portions, and, sensing the density of the fluid being driven out of one or more of the primary and auxiliary containers and stopping the driving upon sensing of a change in the density.

In accordance with the invention there is also provided a method of separating and processing a biological fluid comprising materials of differing densities in a centrifuge system having a plurality of blood processing containers interconnected by fluid flow tubing, the fluid flow between containers being controlled by one or more electrical or electromechanical devices, the method comprising:

disposing a selected biological fluid comprising two or more materials of different densities in at least one of the containers;

mounting an electronic data processing mechanism in the centrifuge, the electronic data processing mechanism having instructions for controlling operation of one or more of the electrical or electromechanical devices;

spinning the containers and the mounted electronic processing mechanism in the centrifuge to separate the biological fluids within the at least one container into different layers;

controlling removal of one of the layers from the at least one container by use of the instructions while the electronic data processing mechanism is being spun. As can be readily imagined, any one or more other functions as described in this application can be carried out and controlled by the spinning electronic data processing mechanism in any predetermined or preprogrammed sequence while the blood processing operations are being carried within the spinning centrifuge.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

FIG. 2A is an enlarged detail view of the area encircled by arrows 2A-2A on FIG. 2

DETAILED DESCRIPTION

Figure 2:
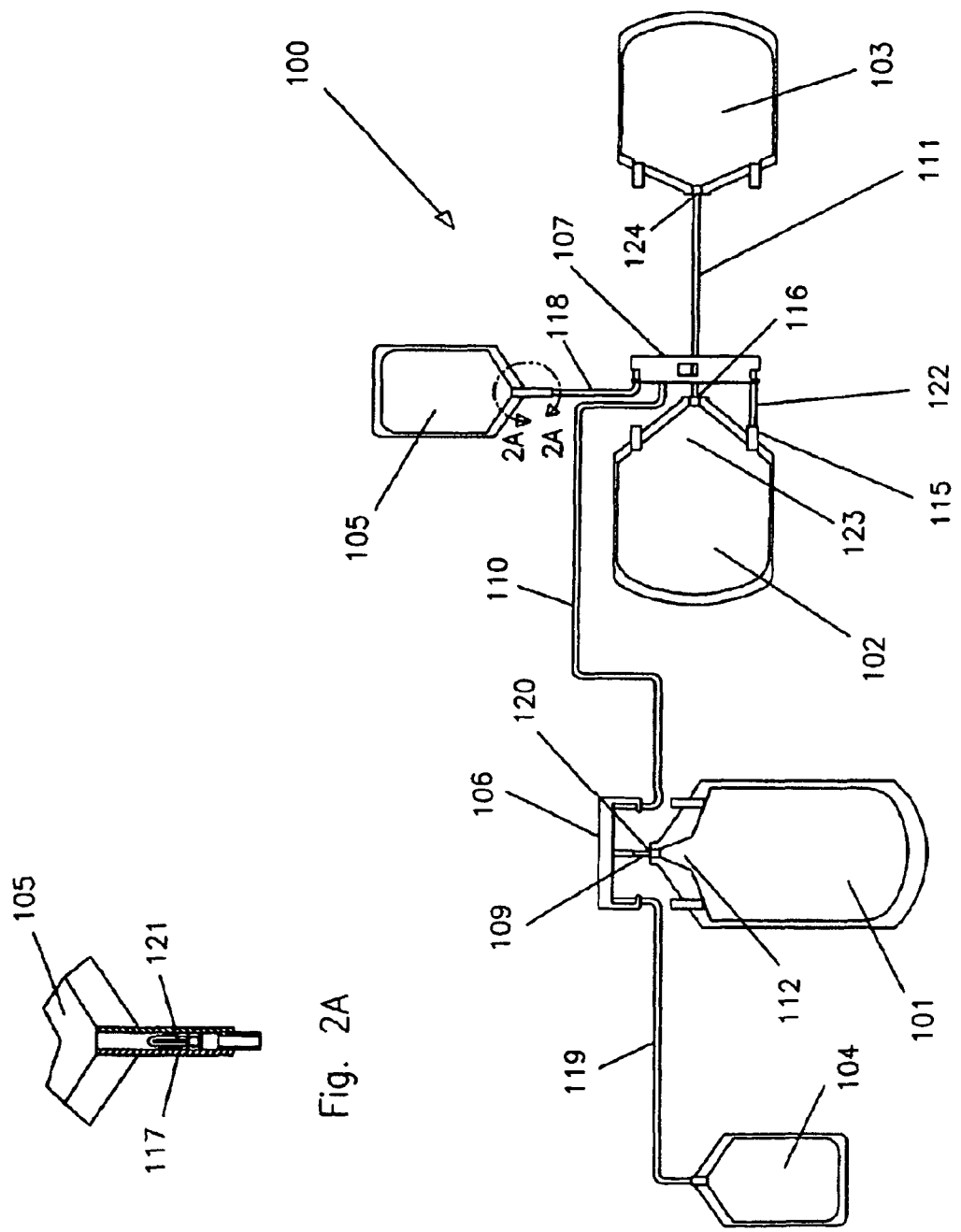
FIG. 2 is a schematic view of a disposable set of blood processing containers or bags.

Referring to FIG. 2, a disposable set of blood processing bags or containers 100 is used to collect blood from a normal donor using standard blood collection method. A phlebotomy needle (not shown in FIG. 2) is inserted in the donor's vein and blood is allowed to flow from the needle through a tube connected to the primary bag 101. When desired amount of blood is collected in the primary bag, the tubing connected to the needle is heat sealed and disconnected from the set.

Figure 17:
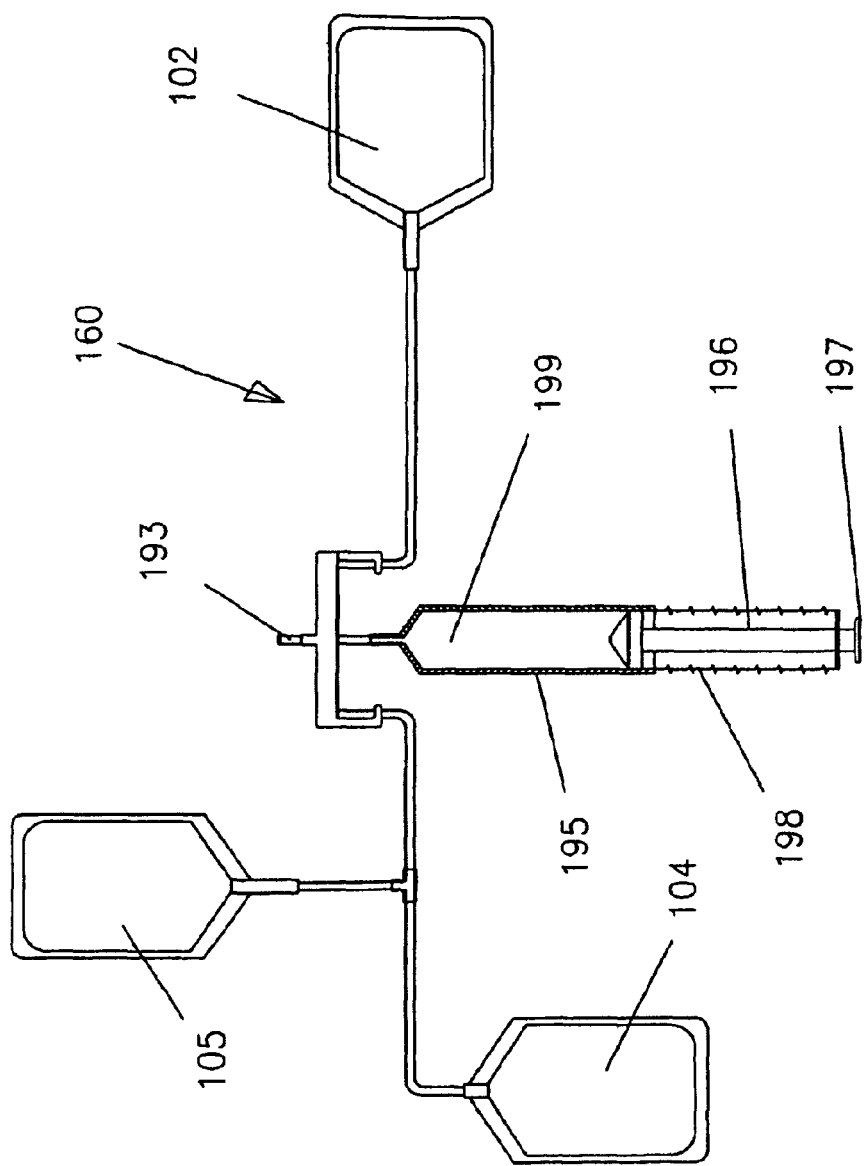
FIG. 17 is a schematic view of a disposable set of blood processing containers including a syringe for use in a system according to the invention.

FIG. 17 shows a schematic view of a syringe blood processing disposable set. The blood processing set 100 is comprised of a primary bag that is interconnected to multiple satellite bags. All primary and satellite bags are preferably made of flexible plastic material. In FIG. 2, the primary bag 101 is connected to RBC manifold 106. The RBC manifold 106 is preferably made of rigid plastic. It has one inlet that receives the flow exiting the primary bag 101 through tubing 109, and two outlets. One outlet directs the flow to the plasma manifold 107 through a connecting tube 110, and the other outlet directs the flow to the WBC (Leukocytes) bag through a connecting WBC tube 119.

The plasma manifold 107 is preferably made of rigid plastic. This manifold receives plasma through tubing 110 and directs it to inlet port 115 on the plasma bag. It also receives solution through tubing 118 and drives it to the primary bag 101 through tubing 110. Tubing 111 connecting the plasma bag platelets outlet port 116 to the platelets bag passes through the manifold.

To facilitate the mounting of the blood processing set 100 inside the centrifuge. The set is mounted on chuck 30, which is a detachable module of the centrifuge. This allows a blood bank operator to mount the set 100 to the chuck 30 while the chuck is rested on a bench top.

Figure 3:
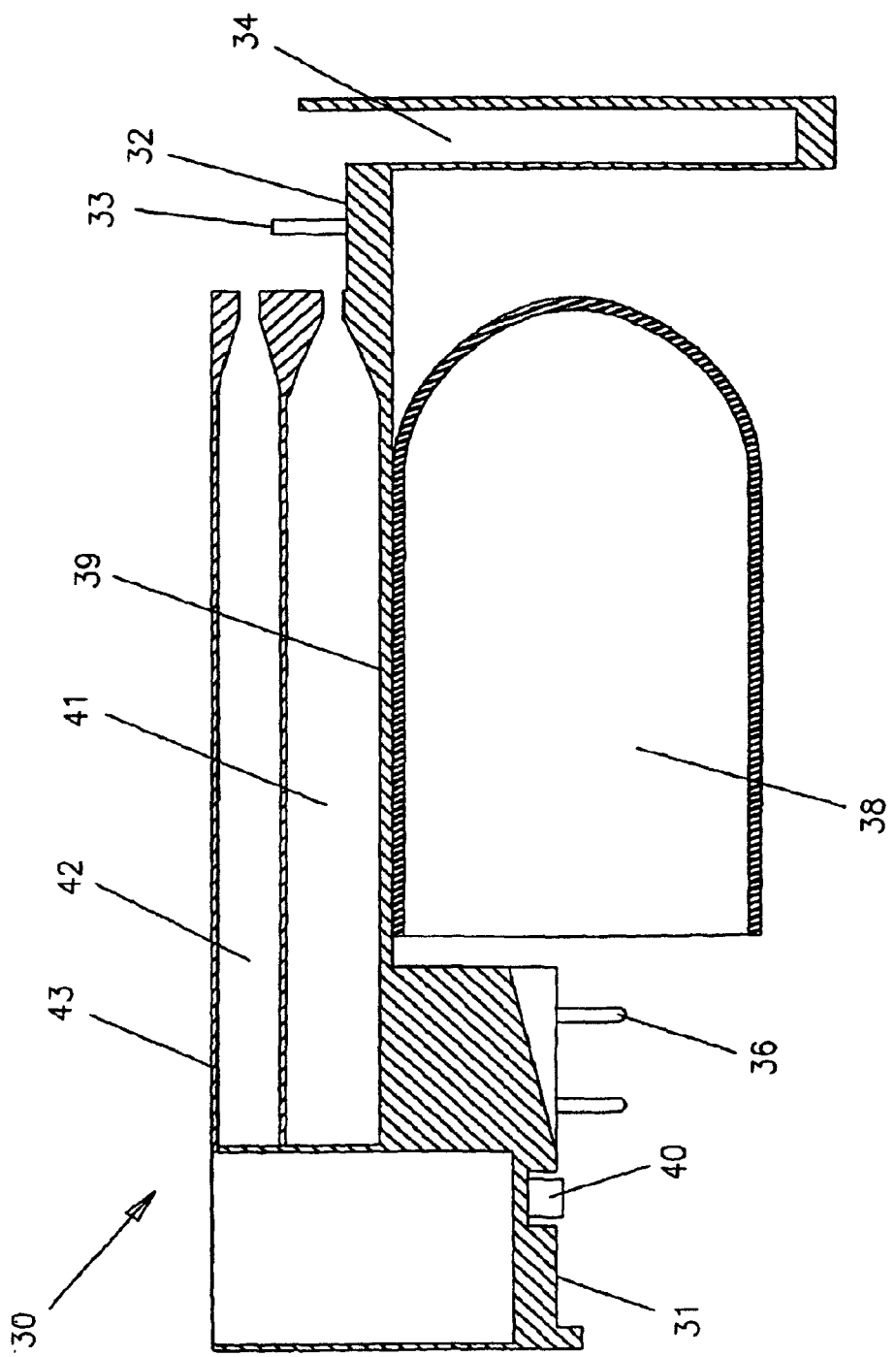
FIG. 3 is a longitudinal cross sectional view of a chuck component of a centrifuge apparatus according to the invention.

Referring to FIG. 3, the operator inserts the primary bag inside the flexible support bag 38 bonded to the bottom plate 39 of the chuck 30. The primary bag is supported by a juxtaposed support bag 38. The RBC manifold 106 is snap fitted inside a special holder 31. This manifold is mounted inside the chuck in one way only. A number of round holes 114 located on bag fins 113 are engaged with pins 36 on the chuck located at the bottom of the chuck between the flexible support bag 38 and the RBC manifold holder 31. Tubing segment 109 that stretches from port 120 on the primary bag 101 to the RBC manifold 106 is rested on a support 40.

The top of the chuck has two chambers located on the top of each other. Plasma chamber 41 is sandwiched between the support bag 38 and the solution chamber 42. The support bag 38 is bonded to plate 39, which is the bottom plate of the plasma chamber 41. The cover door of the plasma chamber contains the solution chamber 42. This cover door is opened to dispose plasma bag inside the plasma chamber, then closed. The plasma bag has only one way to be mounted inside the plasma chamber, where the plasma inlet port 115 and the plasma platelets outlet port 116 are fitted in a matching profile inside the chamber. The cover door 43 of the solution chamber is opened to dispose the solution bag, solution port 117 that contains a breakable seal 121 is fitted in a matching profile inside the chamber (FIG. 2A).

The plasma manifold 107 is snap fitted inside a special manifold holder 32 located on the top of the chuck. This manifold is mounted in one way only setting tubing 110 and tubing 111 in the proper positions. A spring-loaded clamp 33 automatically captures tubing 118 connected to the solution bag 105 as the manifold 107 is snapped in place. The spring-loaded clamp 33 occludes tubing 118 preventing any fluid flow through the tubing. This allows the operator to break the breakable seal 121 at the solution bag port 117. No fluid leaks through the set because tubing 118 is occluded. The WBC bag 104 is also fitted inside chamber 42 along with the solution bag 105; the cover door 43 is closed.

Platelets bag 103 is fitted inside compartment 34 at the back end of the chuck 30.

Figure 4:
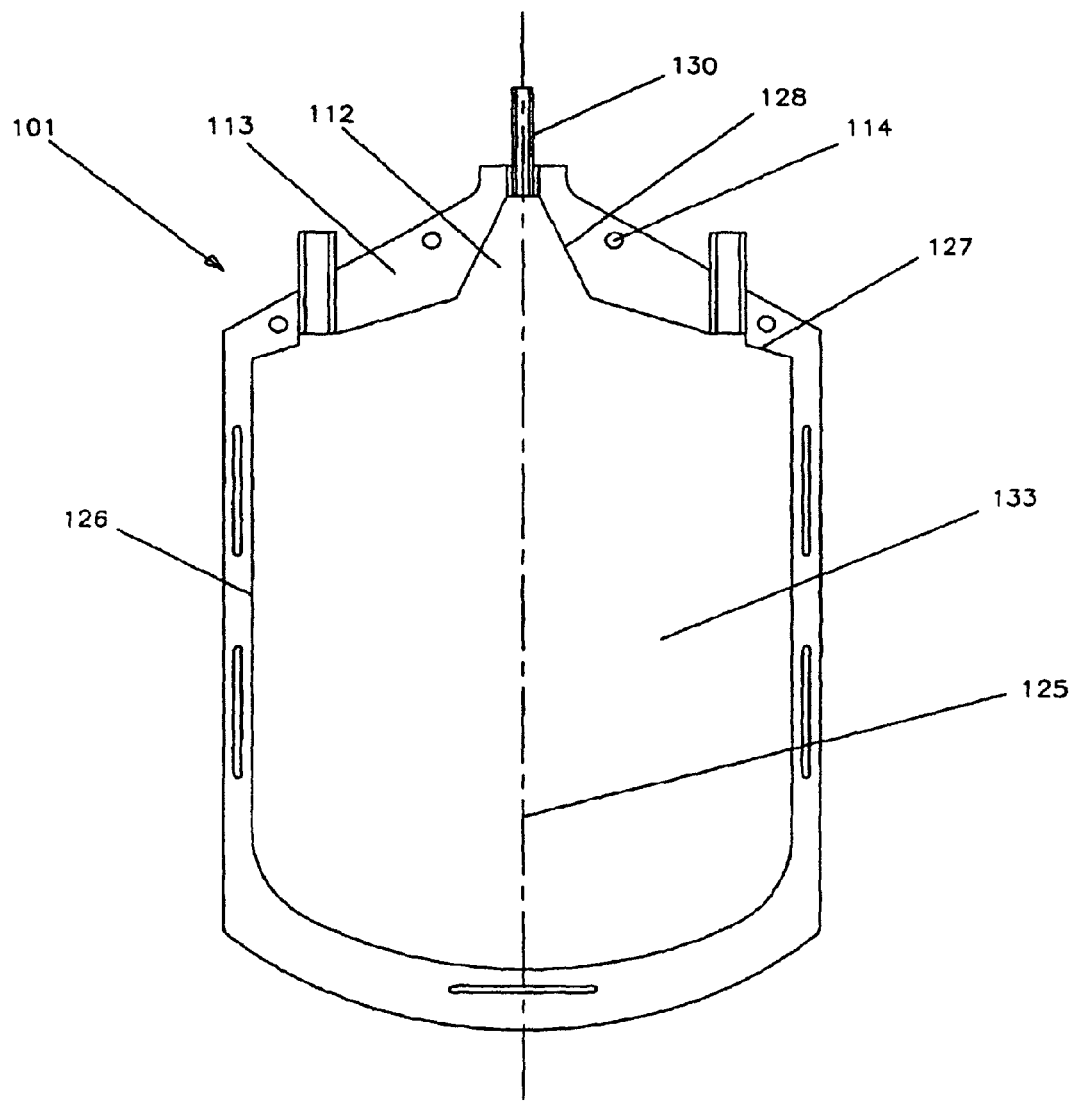
FIG. 4 is a schematic view of a disposable container or bag used according to the invention emphasizing a convergent funnel shaped top edge blending into and with a tapered atrium portion.

Referring to FIG. 4, in the main embodiment containers are made by heat sealing two flexible thermoplastic films. The primary container 101 and at least one satellite container 102 consist of a main chamber 133 attached to a small atrium 112. The main chamber having two edge seals 126 that are generally parallel to the longitudinal axis 125. Each edge seal segment 126 merges into a first tapered edge seal 127 that converges toward the longitudinal axis and leads to the atrium. The atrium 112 is formed by second tapered edge seals 128 that continue from the tapered edge seals 127 of the main chamber. The edge seals 128 of the atrium converge and lead to an exit aperture that is sealably connected to a first conduit or tube 130. This conduit 130 communicates with the interior of the container and functions as an exit port. The container may have other conduits functioning as exit ports located on any surface or edge seal of the container.

The tapered edge seals 127 at the top end of the main chamber provide a converging channel to gently direct the flow to the atrium to be funneled via edges 128 to the exit port. The converging channel in the atrium permits the longitudinal and transversal velocity vectors to have a resultant velocity that streamlines the flow and preserves the separation edge between two layers of different densities formed in the bag or chamber as the edge approaches the exit port.

The angle between the tapered edge seals for the main chamber or for the atrium is anywhere between 10 degrees and 170 degrees. It is preferred to have the angle between the tapered edge seals for the main chamber near 120 degrees, and for the atrium near 60 degrees.

The volume capacity of the primary container is about 600 ml and for the satellite container is about 400 ml. The atrium may have a volume anywhere between 2 ml and 100 ml. The rest is the volume of the main chamber. The preferred volume for the atrium is about 10 ml.

Figure 5:
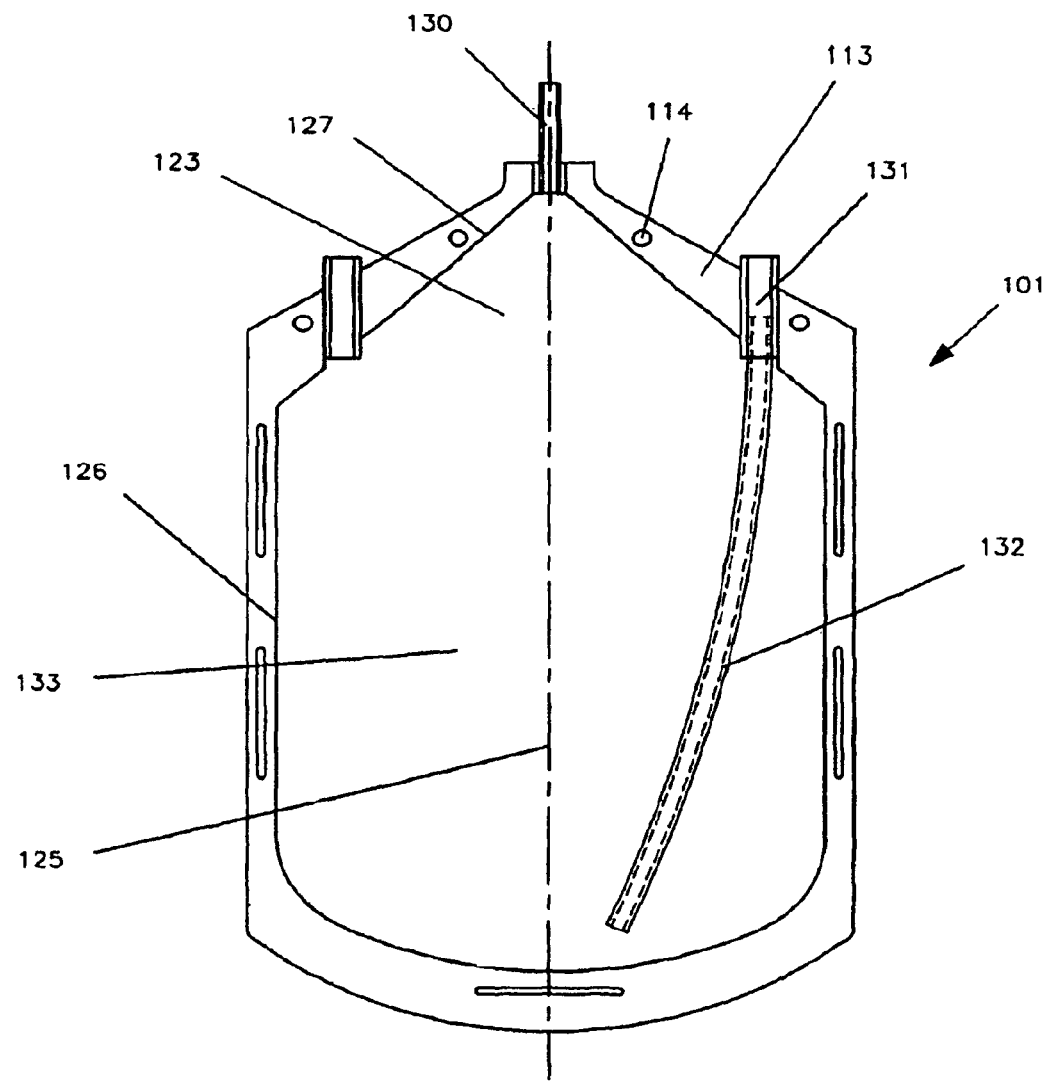
FIG. 5 is a schematic view of a disposable bag emphasizing a convergent funnel top portion merging/blending with an exit port.

Another configuration is demonstrated in FIG. 5 where the primary container 101 and at least one satellite container 102 having two edge seal segments 126 parallel to the longitudinal axis 125. Each edge seal segment is merged with a tapered edge seal 127 converging toward the longitudinal axis and blend with the first conduit at the top end of the container. The tapered edge seals form a convergent funnel 123 inside the bag leading to the exit port. This convergent funnel streamlines the flow and preserves the separation edge between tow layers of different densities as it approaches the exiting port.

In another arrangement for primary or satellite bag, the atrium has two edge seals parallel to the longitudinal axis. These edge seals emerge from the tapered edge seal 127 and merge with another set of tapered edge seals 128 leading to the first conduit on the top end of the atrium.

Another embodiment is also demonstrated in FIG. 5 where the primary container 101 and at least one satellite container 102 having a second conduit 131 communicating with the interior of the container with a tubing segment 132 extending to the bottom of the container. This configuration enables the fluid at the bottom of the container to exit out through the tubing segment.

Figure 6:
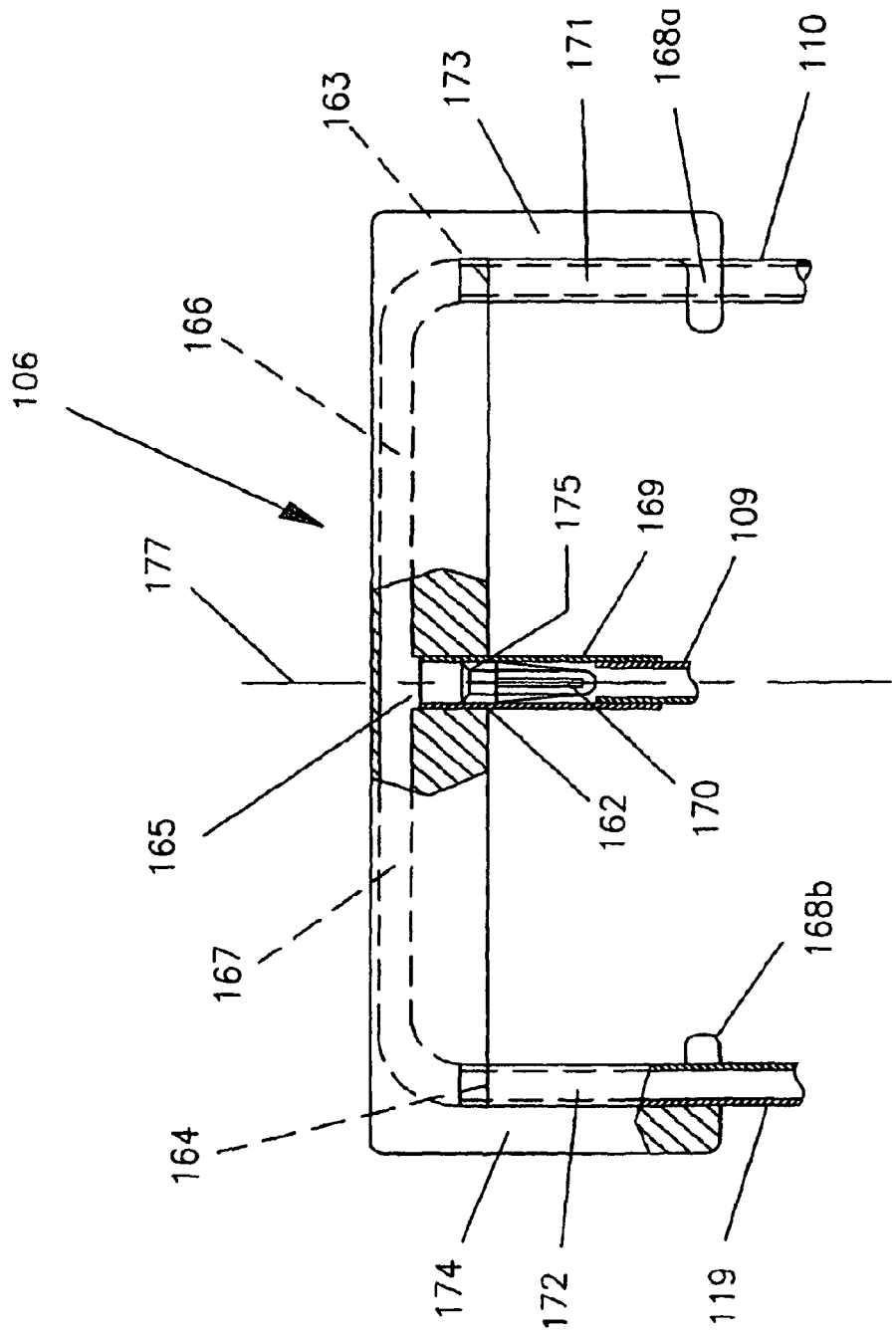
FIG. 6 is a top view of an RBC manifold with a cutout view of a central port with an embedded breakable seal and channels, and a cutout view of tubing in the holder.

A typical manifold in this invention is made of welding two molded parts having grooves and holes that constitute channels and ports when the parts are joined. Referring to FIG. 6, RBC manifold 106 is made by welding two halves that are molded of rigid or semi-rigid medical grade plastic material. The two halves are joined at their matching faces and seal welded. A special channel for fluid flow is formed between the two halves, connecting three ports inside the manifold. Port 162 is formed at the central section of the manifold coinciding with longitudinal axis 177. Channel 165 sets off port 162 then splits in two transversal channels 166 and 167. These channels respectively lead to ports 163 and 164 that are symmetrically located with respect to the longitudinal axis 177. Tube 110 connecting port 163 to port 180 at the plasma manifold 107, is engaged with a tube holder 168a. Tubing segment 171 is a portion of tubing 110 restrained between port 163 and tubing holder 168a, and braced by support 173.

Tube 119 connects port 164 to WBC container, is engaged with a tube holder 168b. Tubing segment 172 is a portion of tubing 119 restrained between port 164 and tubing holder 168b, and braced by support 174.

Tubing 169 having a breakable seal 170 is inserted in the central port 162. A portion of tubing 169 and breakable seal 170 are enclosed in channel 165 inside the manifold in a way placing the breakable neck 175 at the opening edge of the port 162. The inserted end of tubing 169 is opened to channel 165 inside the manifold, and the outer end is connected to tubing 109 that leads to the primary container. The breakable seal 170 blocks fluid flow between the primary container on one side and both the plasma manifold and the WBC container on the other side. Fluid flow between primary container and both plasma manifold and WBC bag is permitted after breaking the neck 175 on the seal 170.

Figure 9:
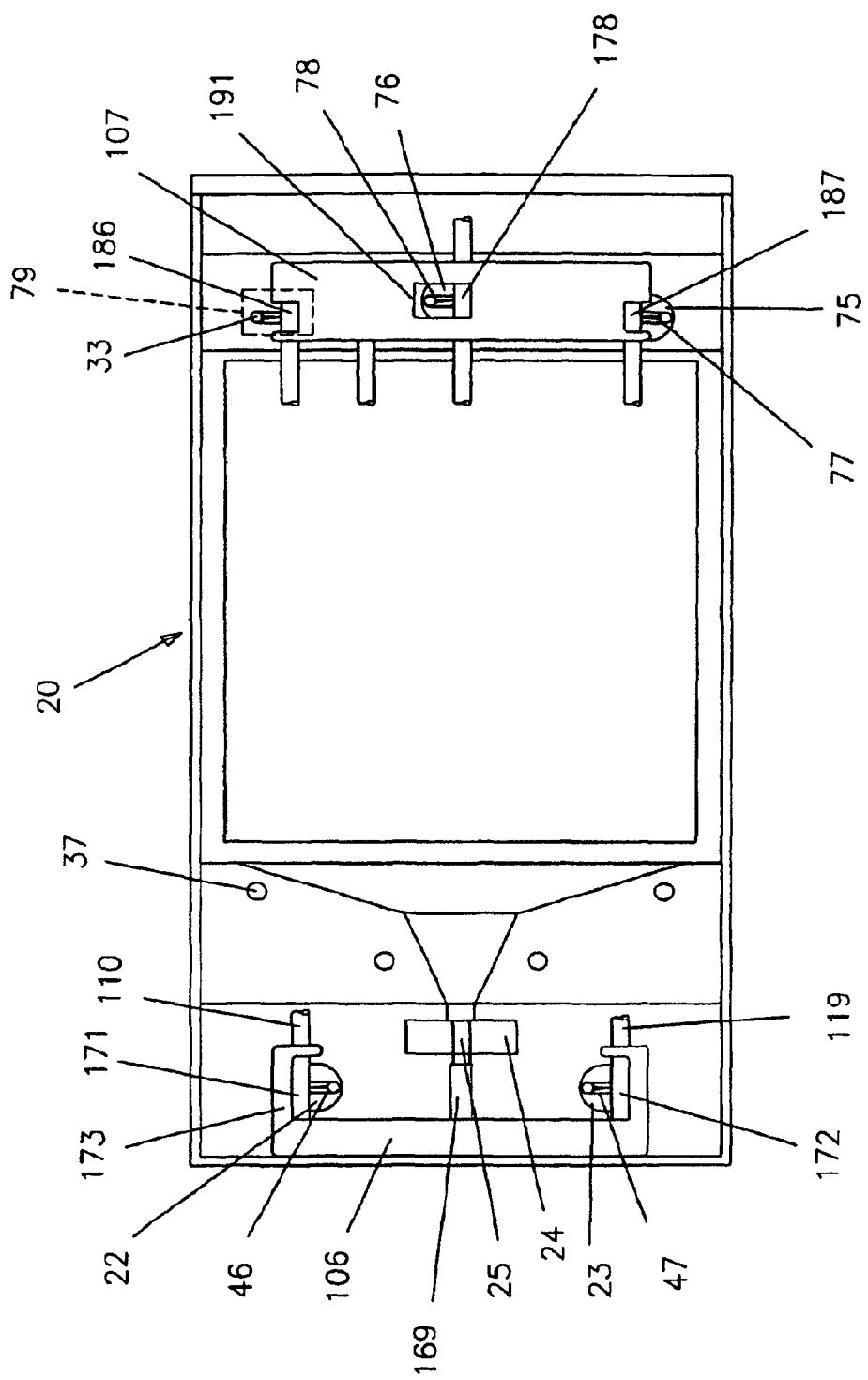
FIG. 9 is a top view of a system according to the invention demonstrating the engagement of RBC and plasma manifolds with the valves and optic sensor on a cradle component of the system.

Manifold 106 is snap fitted in a special manifold holder cavity 31 on the chuck 30. When the chuck is mounted on the cradle 20, RBC valve 22 is engaged with tubing segment 171 and WBC valve 23 is engaged with tubing segment 172 as shown in FIG. 9. Tubing 171 is disposed between RBC valve spoke 46 and support 173. When the valve is closed, spoke 46 toggles firmly toward the support 173 and pinches tubing 171 blocking fluid flow through the tubing. WBC valve 23 having a spoke 47 pinches tubing segment 172 and blocks fluid flow through it. A number of holes 37 are located on the cradle to capture the primary bag holding pins 36 located on the chuck. When a chuck loaded with a processing set is inserted in a cradle, bag holding pins 36 are engaged with the holes 37 on the cradle preventing any possibility for the bag to become loose from the pins on the chuck.

Figure 7:
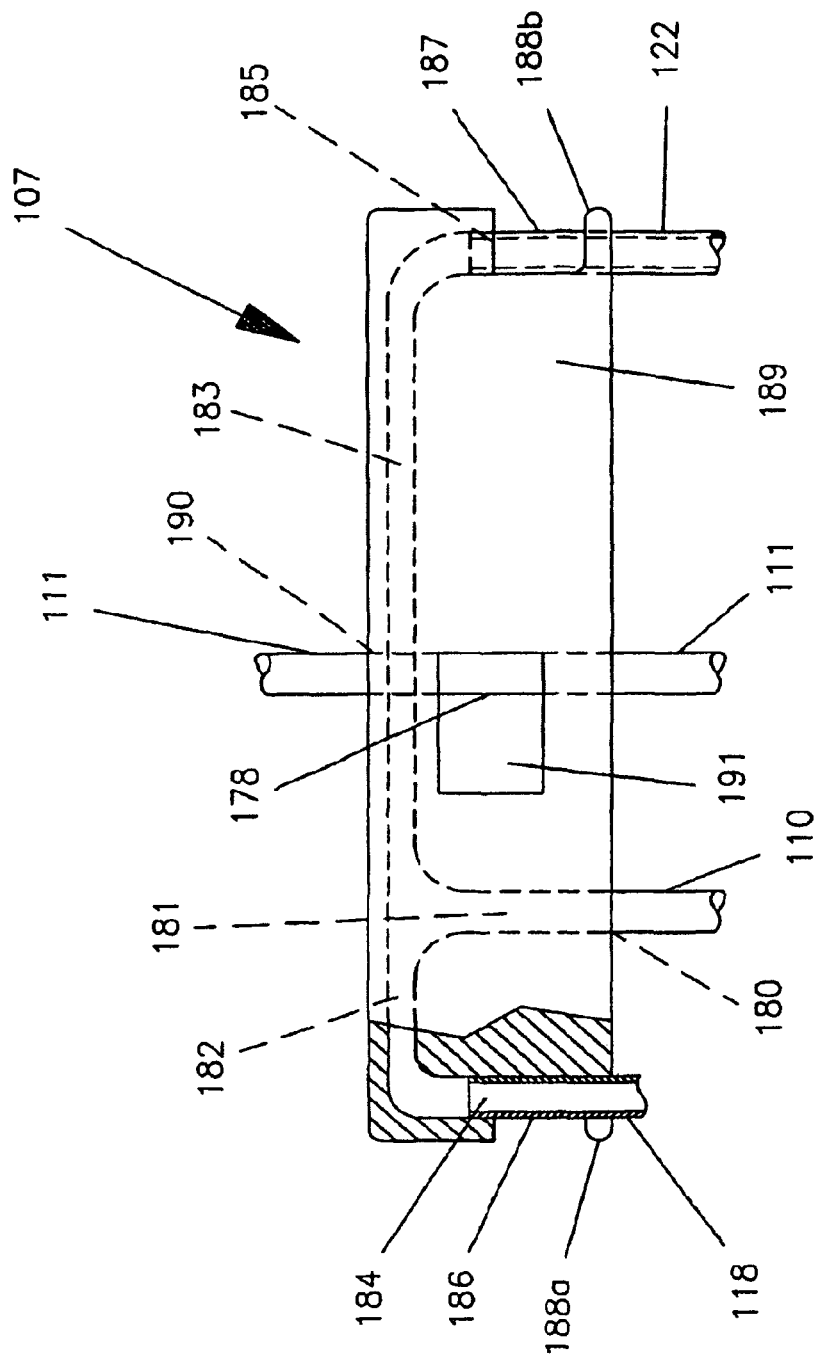
FIG. 7 is a top view of plasma manifold with a cutout view of a port and tubing.

Referring to FIG. 7, plasma manifold 107 is made by welding two blocks that are molded of rigid or semi-rigid medical grade plastic material. As the two blocks are welded to form a manifold, a special channel is shaped inside to distribute a fluid flow. Port 180 is connected to tube 110 originated at port 163 on the RBC manifold 106. Channel 181 sets off port 180 then splits in two transversal channels 182 leading to port 184, and 183 leading to port 185.

Tube 118 connecting the solution container 105 to port 184, is engaged with tube holder 188a. Tubing segment 186 is a portion of tubing 118 restrained between port 184 and tubing holder 188a, and supported by manifold body 189.

Tube 122 connecting plasma container 102 to port 185, is engaged with tube holder 188b. Tubing segment 187 is a portion of tubing 122 restrained between port 185 and tubing holder 188b, and supported by manifold body 189.

Tubing 111 connecting plasma container 102 to the platelets container 103. This tubing is inserted in a groove 190 crossing the bottom surface of the manifold. A cutout window 191 located at the center of the manifold exposing a portion 178 of tubing 111 and clearing for a platelet valve spoke 78 to be engaged with the tubing (FIG. 9).

When plasma manifold is snap fitted in a manifold holding cavity 32, a spring-loaded stem 33 clamps tubing segment 186 and pinch blocks any flow through it. This allows the operator to break the breakable seal 121 at the exit port 117 of the solution container 105 before mounting the chuck on the centrifuge cradle. When the chuck is mounted on the cradle an actuator 79 located on the cradle, is meshed with the stem 33. The actuator activates the stem to open or close the fluid flow path through tubing segment 186. Plasma valve 75 is engaged with tubing segment 187 that is disposed between the valve spoke 77 and the manifold body 189 as shown in FIG. 9. When the valve is closed, the spoke pinch blocks fluid flow through tubing segment 187. The platelet valve 76 is engaged with tubing segment 178 in the same manner through the cutout window 191.

Figure 8:
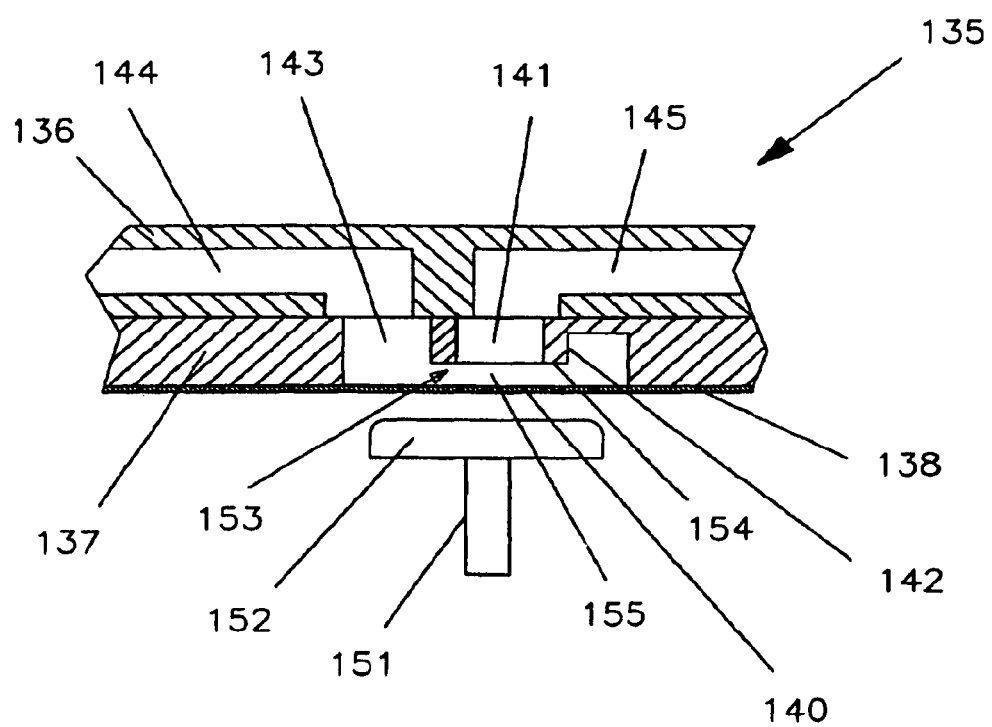
FIG. 8 is a cross sectional view of a diaphragm valve and piston.

In another embodiment, all the valves utilizing a spoke to pinch the desired tubing are replaced with diaphragm valves on both RBC and plasma manifold. FIG. 8 demonstrates a cross sectional view of a typical diaphragm valve 135 that is used in this embodiment. The manifold is made of welding two molded blocks 136 and 137. The diaphragm valve geometry is distributed between the two blocks forming the manifold. Block 137 has a cylindrical shaped depression 153 having two circular orifices 141 and 143 communicating respectively with two separated channels 145 and 144 inside block 136. A flexible diaphragm 140 seals surface 138 of block 137 and prevents any flow outside the manifold or between any two valve depressions. Orifice 141 has a circular wall 142 with a flat and smooth bottom surface 154. A gap 155 is allowed between diaphragm 140 and orifice surface 154 to enable fluid flow between orifice 141 and depression 153. A piston 151 having a disc shaped head 152 with a radius larger than orifice 141 radius but smaller than depression 153 radius.

When the valve is open, fluid flow between channels 145 and 144 is achieved through the path defined by orifice 141 that is connected to channel 145, the depression 153, and orifice 143 that is connected to channel 144.

When the valve is closed, piston head 152 firmly pushes diaphragm 140 against orifice wall surface 154 and seals orifice 141 preventing any fluid flow between channels 144 and 145.

In another embodiment all pinch valves and diaphragm valves engaging with a manifold are replaced with a spring loaded stem and actuator assembly. This mechanism of a separate stem located on the chuck and a mating actuator allow the operator to break all the breakable seals on the processing set after it has been loaded on the chuck and prior to mounting of the chuck to the cradle in the centrifuge.

After loading the blood processing set 100 on the chuck 30 on the bench top, the set and chuck assembly is mounted to a cradle 20 inside the centrifuge. The assembly of the processing blood set 100, the chuck 30 and the cradle 20 is called processing station 60. A rotary table has a number of equally spaced processing stations. Each station processes one unit of blood. Therefore the number of blood units processed in an operation equals the number of stations 60.

Figure 1:
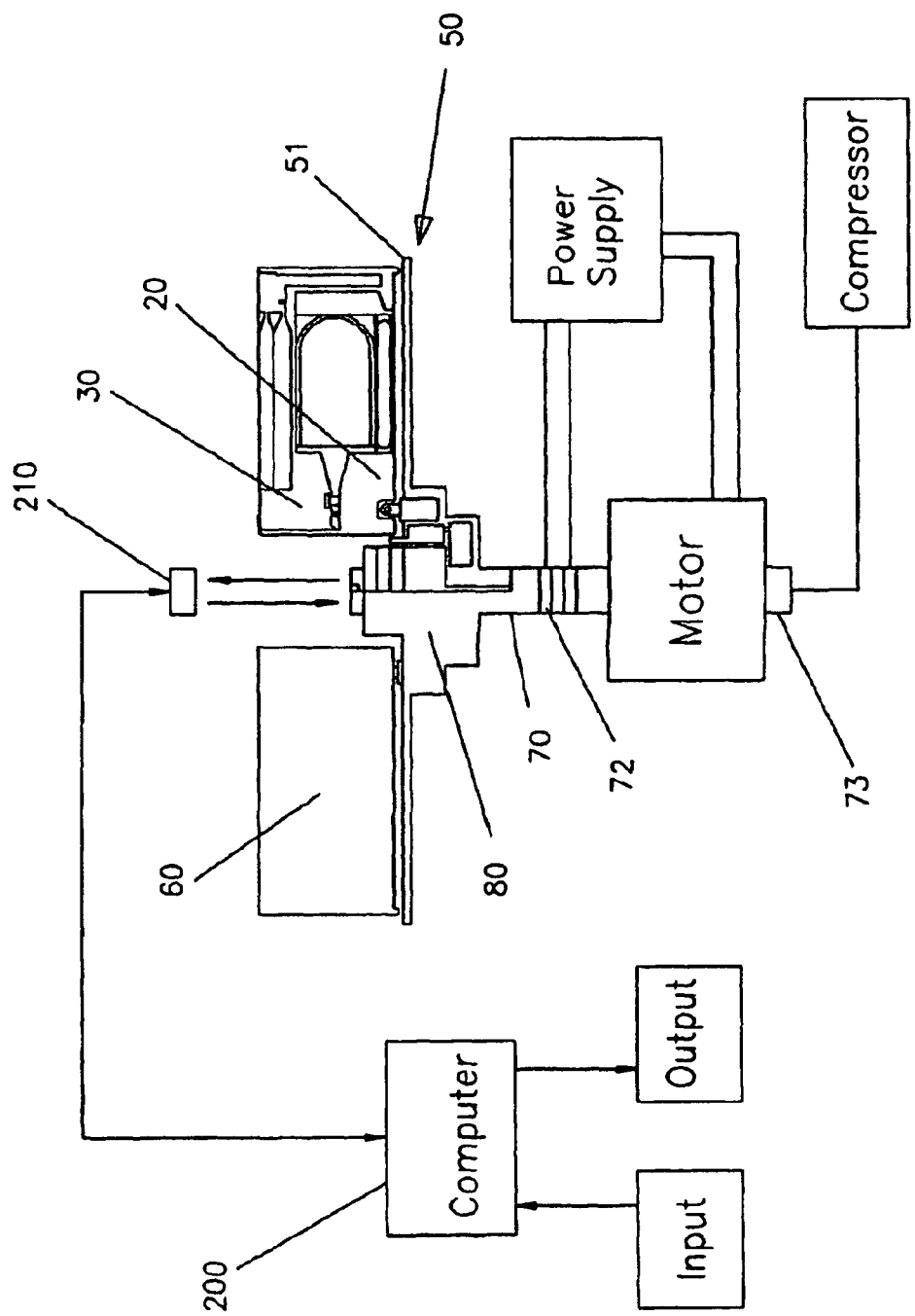
FIG. 1 is a schematic view of blood processing system with rotating table assembly and stationary modules.

A Vertical view of the rotary table 50 is illustrated in FIG. 1. The rotary table 50 compromises of a circular table 51, with chuck 30 fitted in cradle 20, drum 80, and spindle 70. The rotary table 50, the drum 80, and the spindle 70 have an identical axis of rotation. A number of equally spaced cradles 20 are attached to the drum 80 and an identical number of chucks 30, with each chuck fitted inside a cradle rotate with the rotary table around the same axis of rotation.

Figure 10:
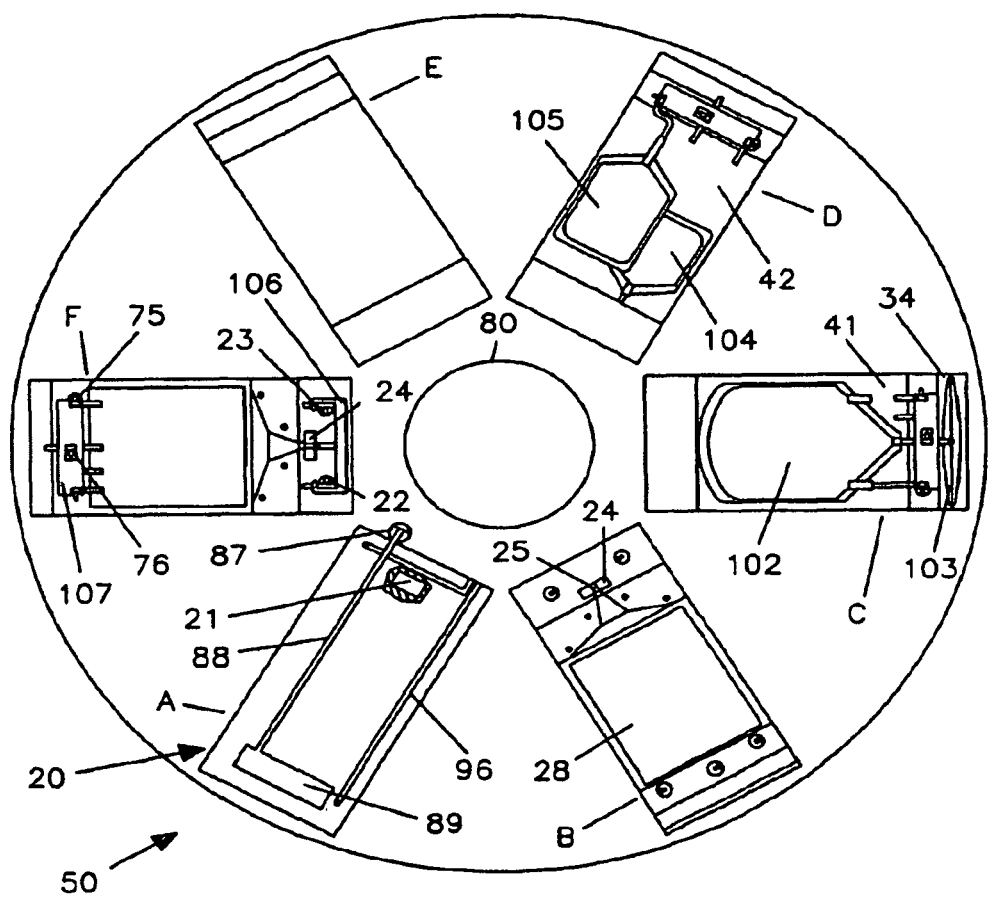
FIG. 10 is a schematic top view of rotating table showing six processing stations with different details of each station being illustrated.

In FIG. 10, a top view of the rotary table 50 is illustrated with a number of cradles 20 and drum 80. It should be noted that six cradles on the rotary table indicated as A, B, C, D, E, and F are for the purpose of better illustration shown in various conditions of assembly. Position "A" demonstrates the self-balancing system with heavy fluid pump 87, hydraulic tube 88, and ballast 89. A window cutout exhibits the hinging of the cradle to a load cell 21. A plurality of air hoses 96 supplying pressurized air to valves and actuators are also shown. Position "B" demonstrates a top view of an empty cradle with a floating rigid plate 28, optical sensor 24 and slot 25. Position "C" illustrates the positioning of plasma bag 102 inside plasma chamber 41 and the placement of platelets bag 103 inside platelets bag compartment 34. Position "D" illustrates the arrangement of solution bag 105 and WBC bag 104 inside solution chamber 42. Position "E" demonstrates a top view of a loaded chuck and cradle assembly ready for a processing operation. Position "F" illustrates the engagement of RBC manifold 106 with RBC valve 22, WBC valve 23, and optical sensor 24. Also the engagement of plasma manifold 107 with plasma valve 75 and platelets valve 76 is shown.

Figure 11:
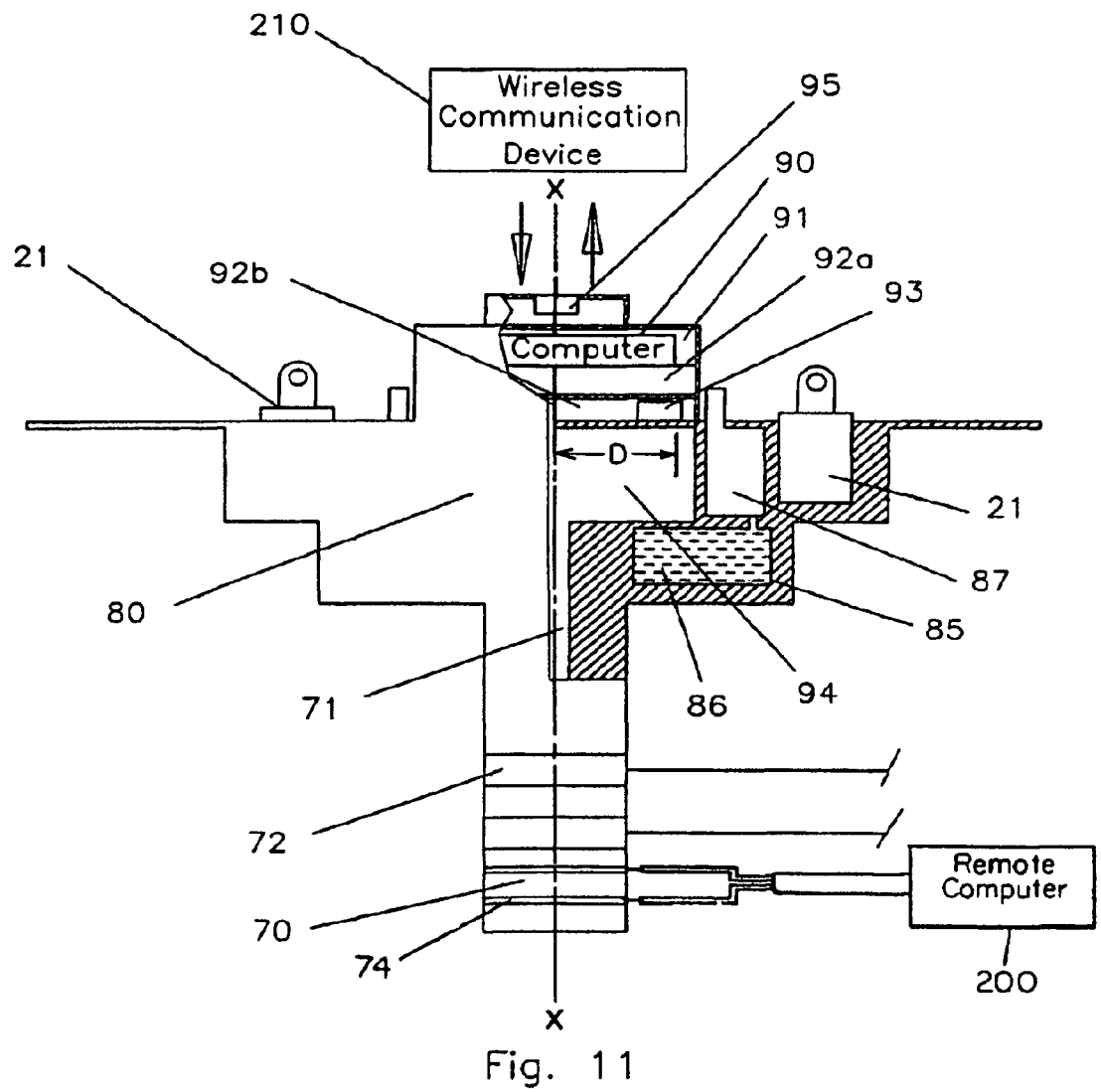
FIG. 11 is an elevated view of a drum and spindle components of a system according to the invention with a cutout view showing detailed modules.

Referring to FIG. 11, drum 80 is rigid and generally cylindrical in shape. It contains electronic boards embedded or mounted in the upper part of the drivably rotatable drum and in close proximity to the axis of rotation. All electronic boards, embedded computer 90, pneumatic board, and drivers are set in small compartments 91, 92a, and 92b filled with epoxy to diminish the effect of the G-force on the electronic components and boards. As shown, all electronic boards are mounted within a distance D radially extending from the axis X of rotation that is less than about 24 inches, preferably less than about 2 inches, most preferably less than about 0.5 inches and even more preferably less than about 0.25 inches. As shown the embedded computer 90, typically a printed circuit board or other microcircuitry device, communicates with a stationary computer 200 that is disposed in a location remote from the rotating components of the system via a hard wire connection such as data cable 81 that is interconnected between the embedded computer and the remote computer via a slip ring. As shown, the embedded computer 90 may be interconnected via a series of slip rings 74 to any one or more of several remotely located devices having electronic or electrical mechanisms such as a compressor 240, power supply 235 or motor 245. Electro-pneumatic miniature valves 93 are secured in a low G-force area. Pressurized air tank 94 is located in the lower part of the drum.

An IR emitter/receiver 95 is placed on the top surface of the drum and at the center of rotation. The function of this emitter/receiver is to have a channel of two way communication between the embedded computer 90 that rotates with the rotary table and a remote stationary computer 200, FIG. 1. A matching stationary IR emitter/receiver 210 is positioned right above the rotating IR emitter/receiver 95 to secure the IR two way communications. The stationary computer 200 on board of the system provides an Input/Output means to the operator. The operator selects the desired protocol or sets the preferred parameters of any particular protocol using standard means to input to the stationary computer 200. The stationary computer analyzes the input and communicates the needed information to the embedded computer 90 in the rotary table using the two way IR communication channel. The embedded computer 90 communicates process information, procedure status, and actual parameter values to the remote stationary computer 200. The stationary computer conveys the needed information to the operator via a monitor, visual display, graphic LEDs, or audio.

The drum contains an array of equally spaced load cells 21 firmly attached to the rotary table. A cradle 20 is hinged to each load cell 21 and is allowed to pivot on the hinge in a radial plane perpendicular to the rotary table.

The drum contains a number of pumps 87 connected to a circular reservoir 85 filled with high density fluid 86. The drum also encloses a pressurized air tank 94 communicating to a stationary air compressor through a lumen 71 entrenched at the center of the spindle 70.

The air passageway extends inside the spindle from a rotary seal at the bottom of the spindle up to the air tank 94 inside the drum 80. A compressor drives compressed air to the rotary seal 73 at the bottom of the spindle (FIG. 1). The air is driven from the rotary seal through air passage inside the spindle and stored in air tank to be used by the pneumatic system.

A number of slip rings 72 are mounted on the rotating spindle to transfer electrical power from a stationary power supply to the electrical components on the rotating assembly. A different slip ring may be used for each type of power (AC or DC) and for each voltage level (5 Vdc, 12 Vdc, etc.)

Figure 12:
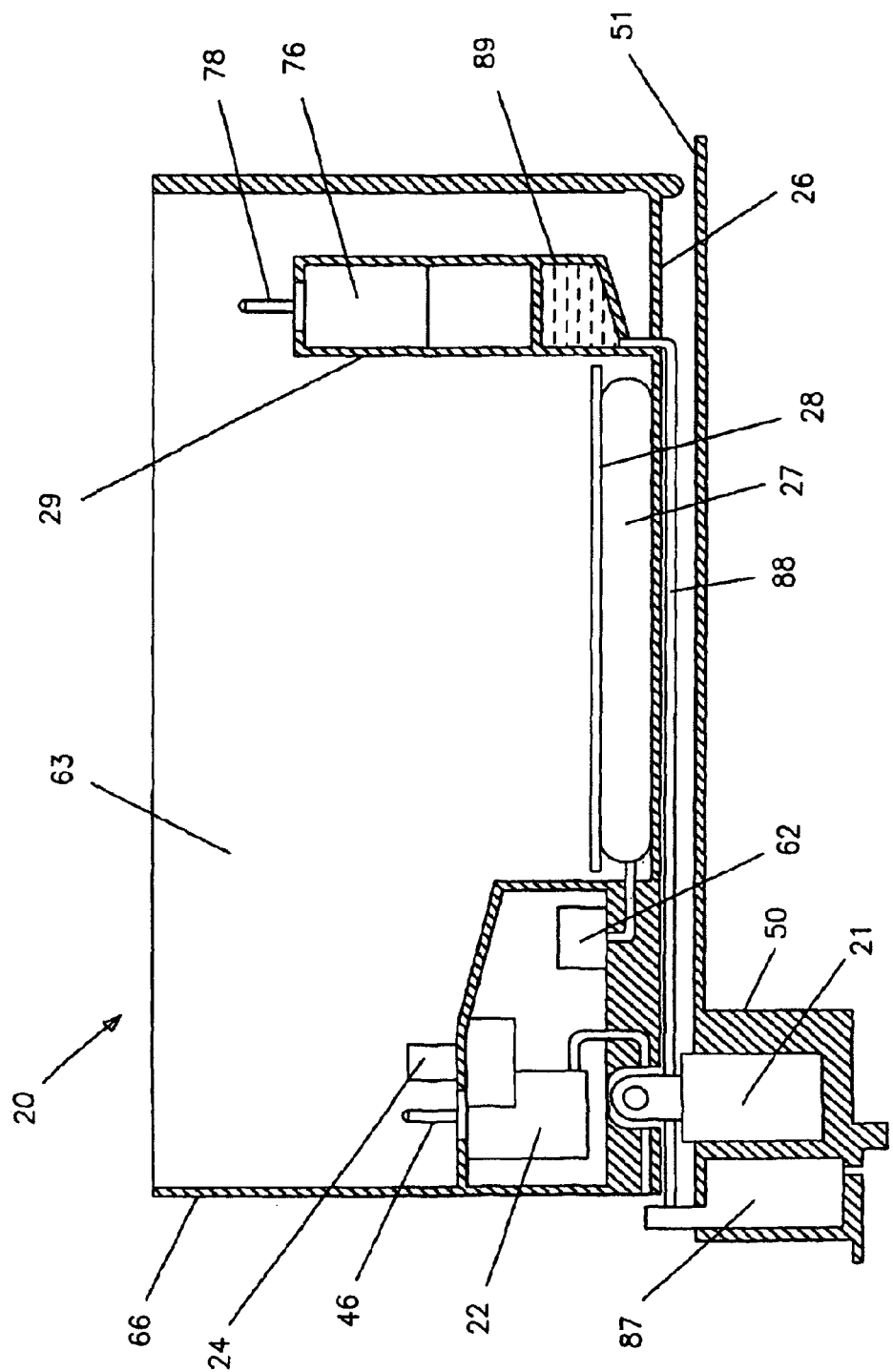
FIG. 12 is a longitudinal cross sectional view of a cradle.

An elevated cross sectional view of a cradle 20 is illustrated in FIG. 12. The main function of the cradle is to embrace a chuck 30 loaded with a blood processing set 100, and to interface the set 100 with the processing equipment.

The cradle 20 is compromised of a rectangular shaped rigid box 66 having rigid sidewalls 63 and rigid base plate 26 that is hinged to a load cell 21 fixed to the rotary table 50. The cradle is allowed to pivot on the hinge in a radial plane perpendicular to the rotary table.

The front part of the cradle that is close to the axis of rotation is profiled to accept a nose funneled primary bag 101. The profile is shaped to match the matting part of the chuck. Holes 37 are positioned to accept primary bag holding pins 36 that are fixed on the chuck. As the rotary table spins, the primary bag tends to move away from the axis of rotation, the flexible support bag 38 and the support wall 29 hold the primary bag in position. The front end of the bag and the atrium part held by pins, are stretched straight preventing any fold or crease that traps RBC near the exit port. Therefore safeguarding product purity.

The front section of the cradle has two pneumatic valves, RBC valve 22 with spoke 46 and WBC valve 23 with spoke 47. This same section has an optical sensor 24 having a slot 25. When the chuck 30 loaded with set 100 is nested in the cradle, valve spokes 46 and 47 are engaged with tubing segments 171 and 172, (FIG. 9). Tubing segment 109 with the help of support 40 is inserted in the optic sensor slot 25.

Figure 13:
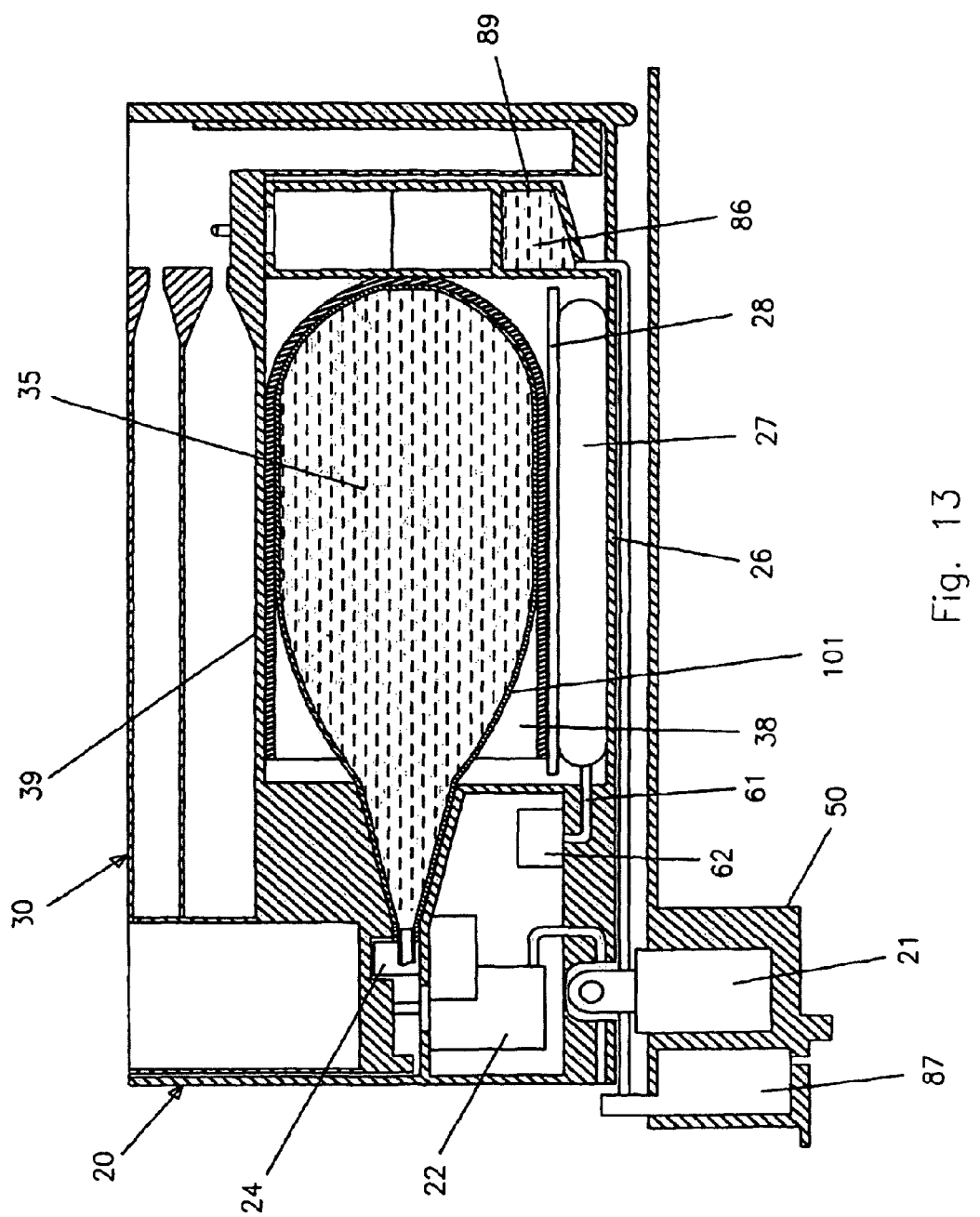
FIG. 13 is a longitudinal cross sectional view of cradle and chuck assembly.

Referring to FIG. 13, the primary bag portion that is fitted inside the flexible support bag 38 is rested on a floating rigid plate 28. The lower surface of plate 28 is bonded to a pressure pad 27. The pressure pad and the flexible support bag 38, containing primary bag 101, are confined between two rigid plates, plate 26 on the cradle and plate 39 on the chuck. Plate 28 bonded to the pressure pad is sandwiched between pressure pad and the flexible support bag that contains the primary bag. This plate is floating and moves vertically with the boundary between the pressure pad and the support bag. The pressure pad is deformable and can increase its volume, depending on the pressure. The volume of the pressure pad increases and plate 28 moves up only when the volume of the primary bag decreases. This compression effect generated by the pressure pad is used to force fluid out of the primary bag. When the pressure is relieved in the pressure pad, plate 28 moves down and easing the compression on the primary bag.

The back end of the cradle farthest from the axis of rotation has two pneumatic valves, plasma valve 75 with a spoke 77 and platelets valve 76 with spoke 78. When the chuck 30 loaded with set 100 is nested in the cradle, valve spokes 77 and 78 are engaged with tubing segments 187 and 178 (FIG. 9). The cradle has a pneumatic actuator 79 that is mechanically engaged with the spring-loaded clamp 33 located on the chuck. The actuator operates the clamp 33 to open or close the flow channel from the solution bag 105 on the chuck 30. Each pneumatic valve and each pneumatic actuator is connected to the electro-pneumatic miniature valve 93 by a pressurized air hose 96. Electro-pneumatic miniature valves are three ports valves. One port is connected to pressurized air tank 94 located in the drum 80, the second port is connected to a pneumatic valve or pneumatic actuator by a pressurized air hose 96, and the third port is open to the atmosphere and used to purge pressurized air.

The embedded computer 90 activates the electro-pneumatic miniature valve, which directs a pressurized air supply from the air tank to the desired pneumatic valve to be activated. When the pneumatic valve needs to be deactivated, the embedded computer controls the electro-pneumatic miniature valve to purge pressurized air from the active valve to the atmosphere.

The cradle has ballast 89 used for dynamic balancing. This ballast is located at the bottom of the cradle and at outermost radius away from the axis of rotation (FIG. 12). A pump 87 is used to drive high-density fluid 86 from a reservoir 85 to the ballast through a hydraulic tube 88.

The main function of this system is to dynamically balance the rotary table at the very beginning of the process to eliminate any cause of undesirable vibration.

The lower part of the drum contains an annular shaped reservoir 85 filled with high-density fluid 86. A number of pumps 87 equal to the number of the cradles 20 are equally spaced around the reservoir 85 and have direct access to the fluid 86. Each pump is used to pump high-density fluid from the reservoir 85 through a hydraulic tubing 88 that extends from each pump 87 and connects to a ballast 89 located at the outer radius of each chuck.

The blood processing sets 100 as they are used to collect blood have their weight distributed over a wide range. The weight of each set is affected by many factors some of which are the volume of the collected blood, the hematocrit of the collected blood, the number of the blood samples taken from the collected unit, the position where the needle connected tubing is disconnected from the set, the tolerance of the solution fluid in the set, and the tolerance of the weight of an empty set. When each set 100 of a random weight is mounted to a chuck 30 that is mounted to a cradle 20 on the rotary table, the weight of each processing station varies. This weight difference on every processing station causes a dynamic imbalance in the rotary table that results in undesirable vibration to the system. Excess vibration to the system negatively affects the separation integrity and therefore product quality. It is preferable if the operator mounts equally weighed sets 100 and chuck 30 assemblies to avoid any vibration issues. However, the rotary table is equipped with a self-balance system. When the rotary table starts rotating at speed enough to lift all processing stations 60 and keep each station held to the rotary table by the load cell 21 only. Therefore the load cell configures the correct weight of the processing station. The difference of weight of each station will be transformed to a difference in the centrifugal force applied on the load cell of that station. Each load cell communicates the applied force to the embedded computer 90. The heaviest station applies the maximum force on the attached load cell. The computer determines the difference between the applied forces at each load cell and the maximum force. This translates to the amount of high-density fluid 86 that needs to be pumped to the ballast 89 of each cradle 20 to bring all the stations 60 to equal weight. This process is completed within the first minute after the start of the rotation of the rotary table.

Reservoir 85 is common to all pumps 87, when any pump drives fluid 86 from the reservoir to the attached ballast; the fluid remaining in the reservoir is evenly spread inside the reservoir to maintain the dynamic balance of the rotary table.

The embedded computer 90 instructs an electro-pneumatic miniature valve to direct compressed air from the air tank 94 to pressurize the pressure pad 27. A pressure sensor 62 is mounted in line with air tubing that connects the electro-pneumatic miniature valve to the pressure pad. Pressure sensor 62 provides feedback to the embedded computer about the pressure level inside the pressure pad (FIG. 12). Based on the sensor feedback, the embedded computer determines when to supply or block the flow of the pressurized air.

The cradle 20 has a shape complementary to, as shown a rectangle box that fits, the chuck 30. When the chuck is nested inside the cradle, sidewalls surround the chuck from three sides. The cradle supports the lateral sides and the backside of the chuck. The front side of the chuck snaps in the cradle to ensure a complete immobility of the chuck with respect to the cradle. A lock is activated manually or by the embedded computer 90 to secure the chuck to the cradle before the rotary table starts to rotate. A micro switch is used to ensure the lock is engaged. The lock can only be engaged when the chuck is seated correctly in the cradle. The micro switch communicates the status of the lock to the embedded computer. The start of the rotation of the rotary table is contingent on a secured lock. When the lock is secured the chuck is firmly held in the cradle, does not move in any direction and never lifts up or separates from the cradle.

This invention discloses automated methods for blood processing including blood components separation and segregation in separate containers followed by treatment of blood component with therapeutic solution. Depending on the protocol selected by the operator, blood separation process range from initial separation of PRP and RBC to a complete separation and segregation of all components, RBC, Plasma, Platelets, and Leukocytes (WBC).

Treatment with therapeutic solution include but not limited to adding additive solution to concentrated RBC, washing concentrated RBC with saline, glycerolize concentrated RBC, mix concentrated RBC with glucose solution, wash concentrated platelets with saline, rejuvenate concentrated RBC.

The method of separating blood and segregating components in separate containers starts by spinning the centrifuge rotor at relatively low speed to dynamically balance itself. The rotor picks up speed (soft spin) to generate centrifugal force about (2000 g) for about 3 minutes enough to separate PRP and RBC in the primary bag and a distinctive sharp separation edge is formed between the two layers. The higher density RBC layer is deposited at the radially outer section of the bag. The lesser density PRP is accumulated in the section closer to the axis of rotation.

Compressed air is admitted to pressure pad 27 to inflate it and to push plate 28 in the upward direction pressuring the primary bag. A pressure sensor 62 inline to the air tubing 61 that feeds compressed air to the pressure pad, monitors the pressure inside the pressure pad. This sensor constantly conveys the pressure level in the pressure pad to the embedded computer 90. As the pressure reaches certain level, RBC valve 22 and plasma valve 75 are opened and the PRP is squeezed out of the primary bag and flows into the plasma bag. Optic sensor 24 monitors the fluid exiting port 120 at the primary bag, and signals to the embedded computer when it detects a change in the exiting fluid density, or when it detects RBC. Plasma valve 75 and RBC valve 22 are closed. The pressure pad volume is diminished by partially decreasing the pressure. This relieves the primary bag and allocates more space for it to occupy. The packed RBC inside the primary bag are moved away from the axis of rotation by centrifugal force, generating a vacuum inside the primary bag, more particularly in the atrium 112. A suction effect is generated as the RBC valve is opened. Fluid inside the tubing 110 connecting the primary bag to the plasma bag is sucked back to the primary bag. It is preferred to open the plasma valve for a fraction of time allowing some plasma to flow back from the plasma bag to the primary bag and flushing the whole connecting tube 110 from any RBC residual.

All valves are closed and the pressure pad is inflated to squeeze the primary bag. The centrifuge spins at higher speed (hard spin) generating centrifugal force about (7000 g) for about 7 minutes.

Blood components in the primary bag are separated to a concentrated RBC layer, a thin buffy coat layer, and small plasma layer. The high centrifugal forces generated by the hard spin, further increases the concentration level of the RBC layer. Therefore, extracting more plasma from the RBC layer. Also the high g-forces separate leukocytes and platelets from the RBC layer and lump them in a buffy coat layer. The RBC layer is amassed in the section of the bag farthest away from the axis of rotation. The buffy coat layer is rested against the RBC layer. The least density plasma layer is situated closer to the axis of rotation. Pressurized air inflates the pressure pad to press the primary bag. RBC valve 22 and plasma valve 75 open and the plasma is pushed from the primary bag to the plasma bag 102 until optical sensor 24 detects a change in exiting fluid density. Valves 22 and 75 close immediately and WBC valve 23 opens to direct the buffy coat (mostly leukocytes) through tubing 119, to the WBC bag 104. It is preferred to allow some time for the buffy coat layer to amass itself near the exit port before opening the WBC valve. The WBC valve stay open for a period of time enough to ensure that the buffy coat layer is displaced to the WBC bag.

The buffy coat volume is about 6 ml on average. After a hard spin and having the pressure pad pressing on the primary bag, the entire buffy coat is accumulated in the atrium 112 portion of the bag, next to the exit port 120.

To ensure the displacement of the entire buffy coat, it is preferred to drive along with the buffy coat, few milliliters of RBC layer that are adjacent to the buffy coat and may contain high concentration of trapped WBC. It is important not to waste too much RBC in this process and limit RBC loss to less than 10 ml. It is equally important to keep a balance between the volume of the leukocytes that are removed from the RBC layer and the volume of the RBC wasted in the process.

In order to optimize the process of leukocytes removal, the buffy coat displacement is accomplished in a series of intermittent spurts. Each spurt transfers about 1 ml of fluid out of the primary bag. The intermission between consecutive spurts is set to allow the buffy coat layer to be reshaped and the separation edge between RBC and buffy coat to be razor-sharp again. During the intermission, it is preferred for the centrifuge to go in a cyclic mode of alternating rotor speed and pressure pad volume to agitate the fluid in the primary bag and release any trapped leukocytes in the RBC layer. This practice may include complete stop and start of the centrifuge and complete retraction and expansion of the pressure pad. After ending fluid agitation and releasing trapped leukocytes from RBC layer, the rotor boosts the speed and ensures the formation of the separation edge between the RBC and the buffy coat before displacing another spurt of buffy coat to the WBC bag.

The optic sensor 24 monitors the density of the exiting fluid and forwards the data to the embedded computer 90. The computer traces a density curve and tracks the changes by calculating the slope of the curve. The computer ensures the continuation of the buffy coat removal process until the density curve slope reaches or exceeds a predetermined value, after which the computer allows certain number of spurts, and then terminates the buffy coat removal task. Since each spurt displaces about 1 ml of fluid from primary bag to WBC bag, the computer 90 ends the buffy coat removal task when certain number of spurts is achieved.

After the centrifuge completes a hard spin for about 7 minutes, the PRP inside the plasma bag 102 is separated to platelets layer and plasma layer. The higher density platelets are sedimented in the radially outward section of the plasma bag, and the plasma is situated closer to the axis of rotation. The plasma bag 102 is mounted on the chuck 30 with exit port 116 is pointed radially outward. The convergent funnel 123 portion of the plasma bag that blends with exit port, is filled with higher density platelets concentrate.

Platelets bag 103 is disposed in a compartment 34. Said compartment is positioned at the outer radius of the chuck in a way that the whole platelets bag is located at a greater radius as compared to the plasma bag exit port radius. Platelets valve 76 occludes tubing 111 connecting plasma exit port 116 to platelets bag 103. At the end of the hard spin, valve 76 is opened and the platelets exit the plasma bag and rush through tubing 111 to end in to the platelets bag by the centrifugal force. The embedded computer 90 controls valve 76 by opening it for a period of time enough to let all platelets and about 50 ml of plasma to transfer to the platelets bag.

In order to remove all platelets efficiently from the plasma bag, it is preferable to open and close the platelets valve 76 intermittently until all platelets exit the plasma bag in small bursts of 1 ml of platelets concentrate. As it is explained in the teaching above, intermittent opening and closing of the valve allows the platelets layer to be reshaped and enhances the sharpness of the separation edge between plasma and platelets. This practice keeps on accumulating high concentration of platelets at the exit port ready to exit the plasma bag when the valve is opened. After completing certain number of platelets valve opening and closing cycles that ensures the depletion of platelets in the plasma bag, the volume of the fluid that exits at each cycle is increased. The valve continues with the intermittent open and close cycles, but the exiting fluid volume is increased in order to drive about 50 ml of plasma to the platelets bag. This routine permits the residual platelets or residual leukocytes to exit the plasma bag with each portion of plasma that transfers to the platelets bag per cycle.

After separating blood components and isolate each component in an individual bag, centrifuge rotor spins at low speed. At this stage the system is ready to start component treatment task. Depending on the selected protocol the system proceeds with the treatment details associated with the selected protocol.

If RBC treatment for up to 42 days storage is selected, the system proceeds by mixing the RBC concentrate with additive solution.

The pressure is partially decreased in the pressure pad, diminishing its volume. This allocates some space for the primary bag to expand. Solution actuator 79 is activated to open solution clamp 33 that opens the flow channel from the solution bag 105. RBC valve is opened at the same time permitting the additive solution to flow inside the primary bag and mix with the concentrated RBC. The additive solution is driven by the centrifugal force out of the solution bag 105 and siphoned in to the RBC bag by the negative pressure generated by the expansion of the primary bag as explained above.

RBC valve 22 and solution clamp 33 are closed after a predetermined period of time set to permit the required volume of the additive solution to transfer to the primary bag.

If the RBC wash protocol was selected, the system progresses by driving saline to the primary bag to wash the concentrated RBC and then express the consumed saline out of the bag and store it in an empty waste bag or in the original solution bag.

As it is explained in the teaching above, the RBC valve 22 and the solution clamp 33 are opened and the saline is rushed in to the primary bag and mix with the concentrated RBC. The RBC valve and the solution clamp are closed and the centrifuge enters a cyclic mode of alternating rotor speed and pressure pad volume to agitate the fluid in the primary bag to enhance the mixing process between saline and the RBC layer. The RBC valve and the solution clamp are opened and the pressure pad gently squeezes the primary bag to drive the excess saline solution out. The RBC valve and the solution clamp are closed immediately when the optical sensor 24 detects a change in the exiting fluid density in the tubing segment 109.

The same technique explained in the teaching above for RBC wash is used to glycerolize the concentrated RBC. The only difference in this process is that a container filled with 500 ml of glycerol is used to glycerolize the RBC instead of the saline solution bag. The centrifuge goes through the same operating modes and ensures a steady glycerol flow in to the primary bag and a thorough mixing with the RBC layer. Then the excess glycerol is removed from the primary bag and returned to the glycerol container.

Figure 14:
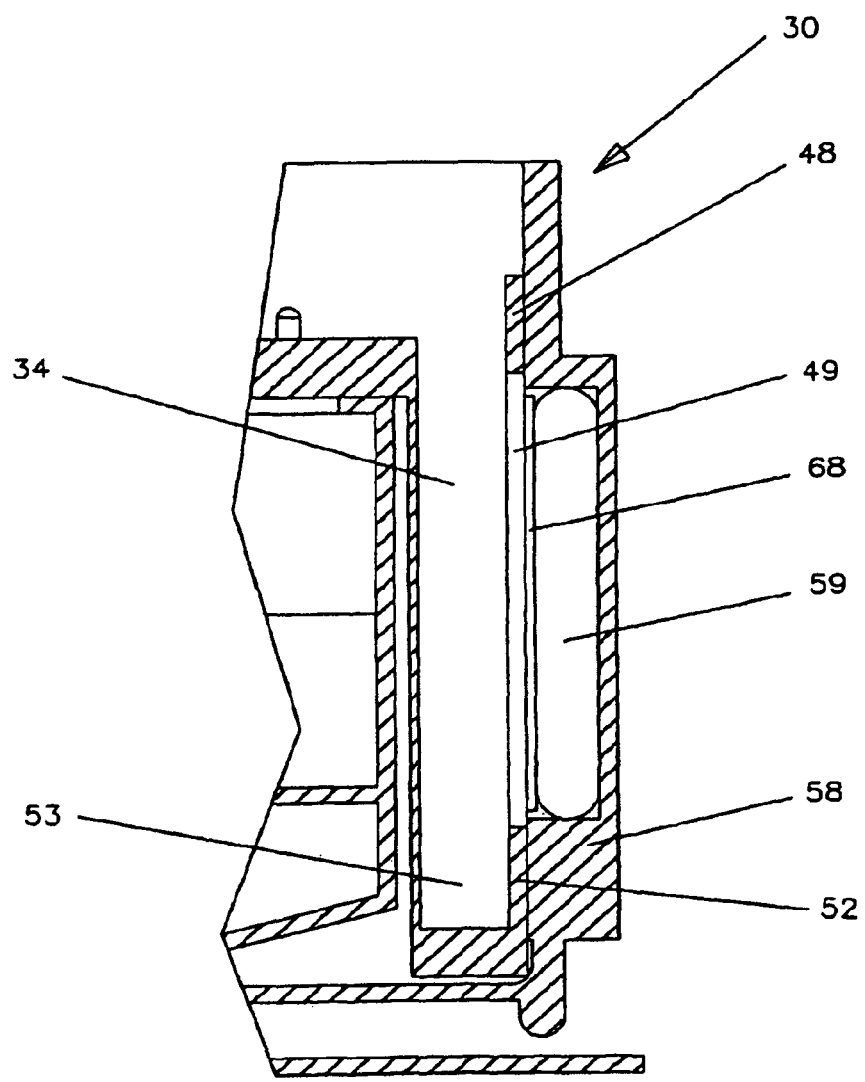
FIG. 14 is a cross sectional view of a pressure pad embedded or mounted in the back wall of a centrifuge system according to the invention.
Figure 15:
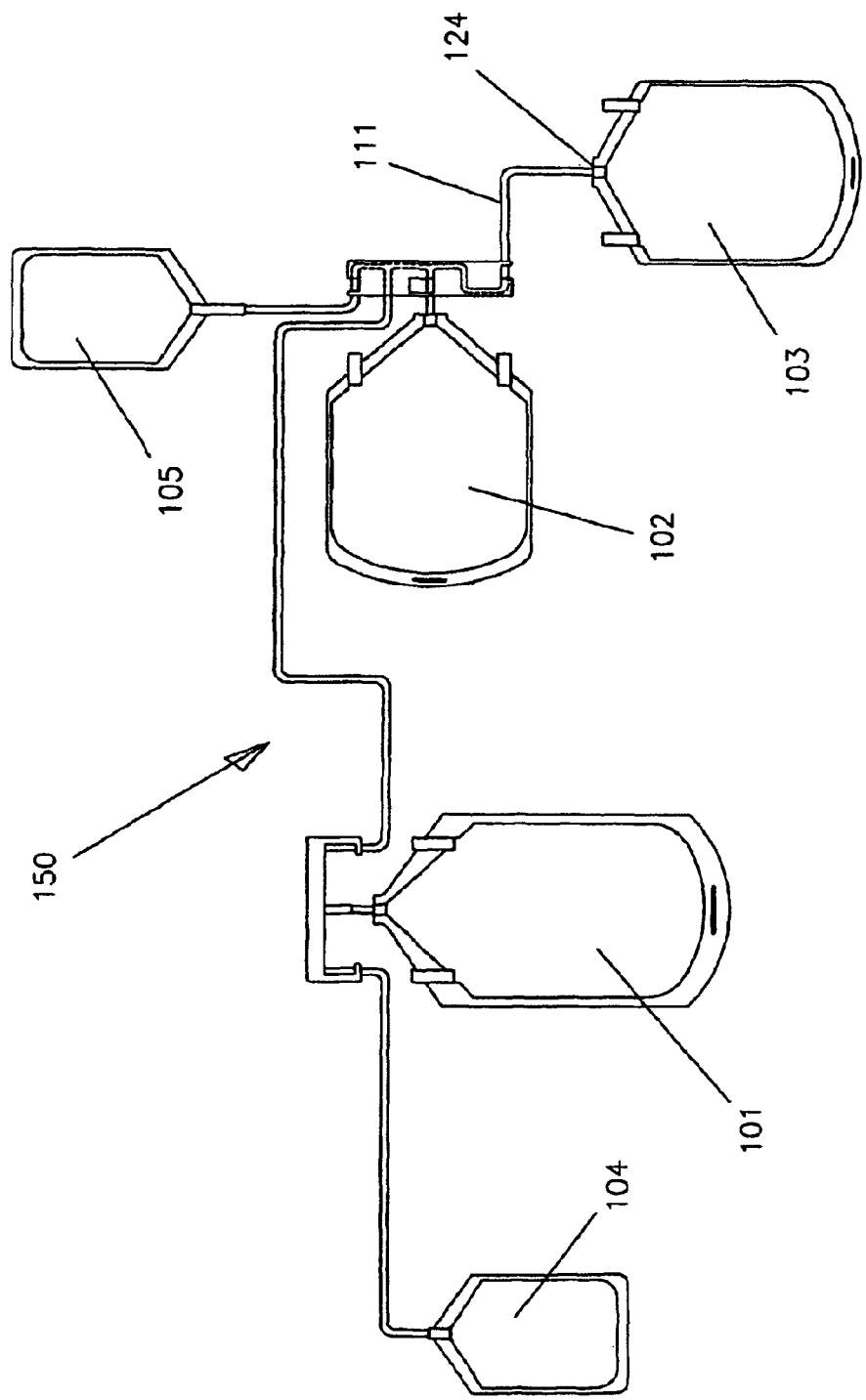
FIG. 15 is a schematic view of a disposable set of blood processing containers or bags.

In another embodiment, illustrated in FIG. 14, the back wall 48 of the platelets compartment 34 has a large window 49. A pressure pad 59 is fitted in cradle back wall 58. This pressure pad 59 is bonded to a rigid plate 68 that matches the window 49 on the back wall of the platelets compartment. When the pressure pad is inflated, it expands into the platelets compartment 34 through the window 49 squeezing platelets bag 103 inside the compartment 34. Window 49 that mirrors the pressure pad is positioned on back wall 48 in a way having the lower section 52 of the back wall intact. When the pad expands through the window, it squeezes most of the upper part of the platelets bag leaving the area 53 that is supported by wall section 52 relaxed. The pressure pad expands from the outermost radius of the compartment 34 and moves inward in the direction of the axis of rotation. As the platelets bag is squeezed radially inward, platelets migrate by centrifugal force to area 53 under the pressure pad near wall 52. The platelets are captured by the centrifugal forces under the pressure pad and kept inside the bag while washing solution or plasma is forced out of the bag. A schematic drawing of the blood processing set 150 used with this embodiment is shown in FIG. 15. In this embodiment, platelets wash is possible in addition to the other functions defined in the other embodiments. After separating the blood and segregating components in discrete bags, if platelets wash protocol is selected, the system progresses by driving saline to the platelets bag to wash the concentrated platelets and then express the consumed saline out of the bag and store it in an empty waste bag or in the original solution bag.

As it is explained in the teaching above, the platelets valve 76 and the solution clamp 33 are opened and the saline is rushed in to the platelets bag and mix with the concentrated platelets. The platelets bag is disposed in a vertical position inside the compartment 34, and port 124 attached to tubing 111 is located at the top of the bag. The pressure pad 59 is inflated to expand inside the upper portion of the compartment 34 through a window 49. The pressure pad squeezes the platelets bag and pushes the upper portion of the bag radially inward. The lower portion of the bag is not pushed or squeezed by the pressure pad and remains relaxed in area 53 protected by the small wall 52. Also the lower portion of the platelets bag is positioned at a relatively larger radius as compared to the upper portion of the bag. All the platelets rush to the lower portion of the bag by the centrifugal force, while the washing fluid is squeezed out of the platelets bag through exit port 124 located at the top of the bag.

Figure 16:
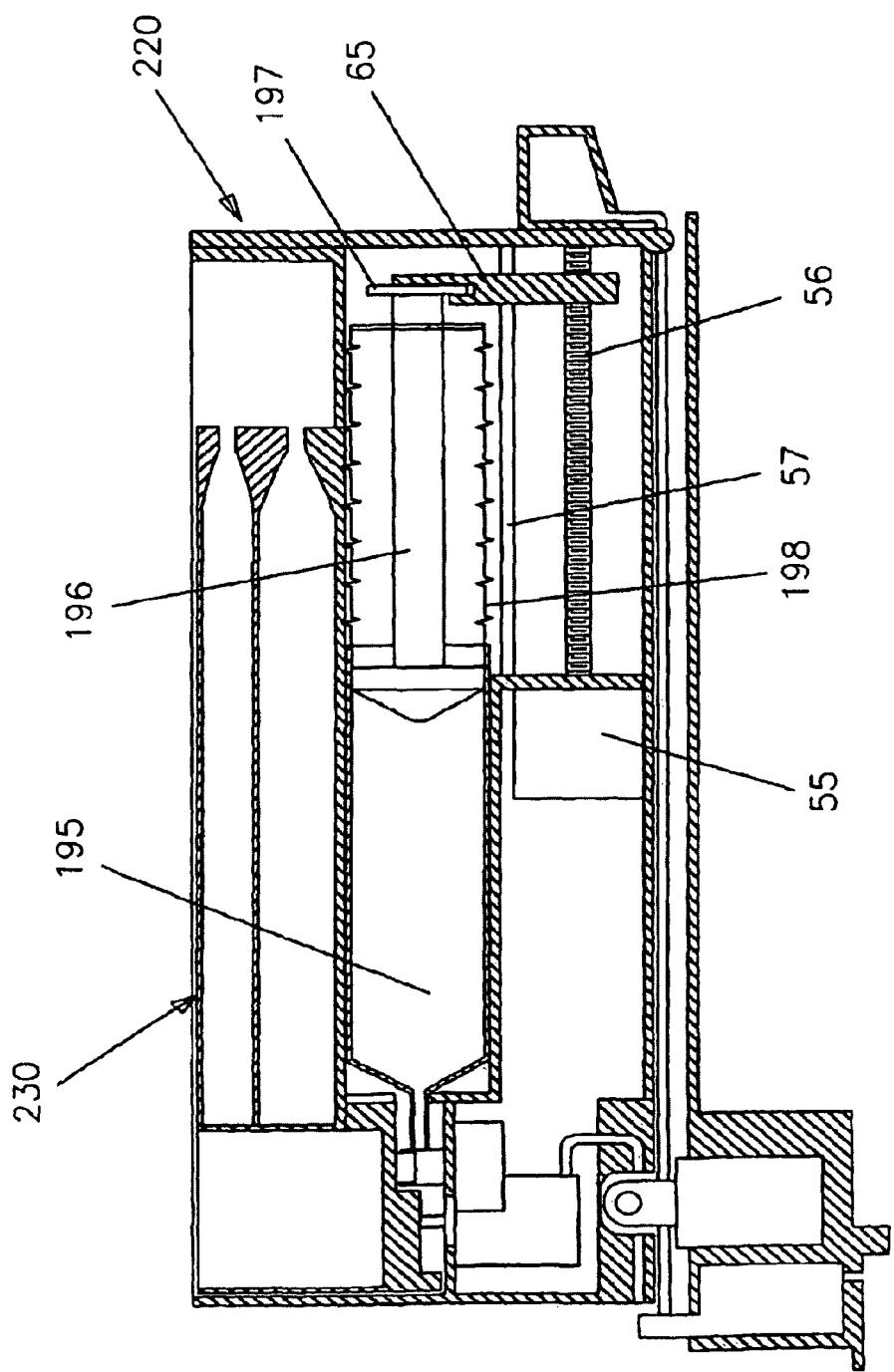
FIG. 16 is a longitudinal cross sectional view of syringe cradle and chuck assembly for use in a system according to the invention.

In another embodiment the blood is provided in a rigid container with a movable sidewall or piston to squeeze fluid out. A schematic drawing of the blood processing set 160 used with this embodiment is shown in FIGS. 16 and 17. In this embodiment, a syringe 195 with a rigid body is used instead of flexible primary bag 101 as mentioned in the preferred embodiment. In many applications a need has been materialized to process a small volume of blood such as umbilical cord blood. An intravenous needle (not shown) connected to the front end of a transfer tubing 193 that is originated at the RBC manifold on set 160. The needle is used to draw blood from a donor or an umbilical cord, and collect it inside syringe chamber 199. After collecting the desired volume of blood, tubing 193 is heat sealed and separated from the rest of the set 160. The set is mounted to a special syringe chuck 230 with the syringe arranged at the bottom. Plasma bag, WBC bag, and the solution bag are boarded in special compartments at the top of the chuck. The syringe chuck and set 160 are inserted in syringe cradle 220. Referring to FIG. 17, a longitudinal cross sectional view of the syringe chuck and matching cradle is demonstrated. The chuck and the cradle embrace syringe 195. Piston handle 197 is engaged with shuttle 65. When step motor 55 is activated, linear screw 56 rotates and sets shuttle 65 in a linear motion along linear slide 57. The shuttle motion presses on the syringe piston 196 forcing the fluid out. Bellows 198 encloses the interface between the piston and the chamber preserving blood sterility despite the movement of the piston.

After a hard spin rotation for the centrifuge, the blood inside the syringe is separated to plasma, buffy coat, and RBC. The step motor activates the piston while the centrifuge is rotating at slower speed. RBC valve is opened, and plasma starts to exit the syringe until the optic sensor detects a change in the exiting fluid density. Plasma is collected in the plasma bag. The piston retreats slightly to recover any cell that could have separated from the buffy coat. RBC valve is closed and WBC valve is opened. The step motor turns slowly pushing the buffy coat to the WBC bag until the optic sensor detects a change in the fluid density. The step motor executes a number of steps before it stops. This ensures the removal of buffy coat cells that could have been trapped y the RBC layer, and sequesters the whole buffy coat in the WBC bag. In case of the umbilical cord blood, the buffy coat is very rich with the valuable stem cells. The WBC valve is closed, and the RBC remain in the syringe. Solution can be added manually by gravity from the solution bag to the WBC bag after removing the set from the centrifuge.

The present invention has numerous applications in the biotechnology and medical fields. In general, the present invention and component separator system design can be applied to any industry where separation is a requirement. Accordingly, examples of such applications include:

Biotechnology

Separation of components from bioreactors and bio-fermentation processes;

Separation and processing of materials in waste management; and

General extraction, purification and concentration of materials for industry use.

Medical

Cell washing;

Enzymatic conversion of red cell to ECO;

Pathogen inactivation;

Glycosylation;

Lipid filtration;

Leukocyte reduction;

Inter-operative cell salvage;

Cryo-preservation;

De-glycerolization;

Blood component separation; and

Aphaeresis (red cell, plasma, platelets).

The embodiments presented are for use for both single blood processing set and for a plurality blood processing sets that operate simultaneously inside one apparatus, when considered with the referenced patents and patent applications. Moreover, a plurality of blood processing sets may be used for one protocol, or each blood processing set follows an independent protocol simultaneously inside one apparatus. Operating protocols are synchronized to maximize efficiency and save time. The computer determines which protocol tasks are executed in parallel and which tasks are executed in sequence such that each blood processing set follows its appropriate protocol in the most efficient manner.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A blood processing centrifuge system, comprising:
    a rotor having an axis of rotation,
    mechanical or electronic means for processing whole blood or blood components within the rotor,
    a computer controlling blood processing operations the computer being mounted to the rotor and spinning therewith,
    the computer mounted to and spinning with the rotor and communicating with a second stationary computer disposed in a remote location from the rotor,
    wherein, the second stationary computer in conjunction with the rotating computer controls the centrifuge system operations,
    wherein said computer and said second computer are managed by software programs that direct the blood processing operations of the blood processing centrifuge system.

2. The centrifuge of claim 1 wherein the mechanical or electronics means are selected from the group consisting of one or more sensors, one or more actuators, and one or more control mechanisms; wherein the control mechanisms are selected from the group consisting of one or more of an electronic circuit, a pneumatic circuit, a wireless communication mechanism, a driver circuit board, a hydraulic circuit, and an electro-mechanical controller.

3. The centrifuge of claim 2 wherein the one or more sensors are selected from the group consisting of a photoelectric sensor, an optic sensor, an ultrasonic sensor and a magnetic resonance imaging sensor.

4. The centrifuge of claim 1 wherein the computer is interconnected by data transmission wires to the second computer disposed in a location remote from the rotor, the rotor including one or more slip rings for enabling the wire interconnection.

5. The centrifuge of claim 1 wherein the computer includes a wireless communication mechanism, the computer interconnected via the wireless communication mechanism to the second computer disposed in a location remote from the rotor.

6. The centrifuge of claim 2 wherein the one or more actuators are selected from the group consisting of a valve, a pump, a motor, a solenoid, a piston, a bellow, linear driver, and electro-mechanical devices.

7. The centrifuge of claim 1 wherein the second stationary computer comprises one or more of a portable computer, a stationary computer, a network of computers, a main frame, a supercomputer, a server, a remote control device, a control panel, a microprocessor, video display monitor or a digital memory device.

8. The centrifuge of claim 1 wherein the computer includes:
    one or more programs that include instructions for executing blood processing operations,
    means for sending and receiving one or more data or instruction signals to and from other devices comprising one or more sensors, monitors, gauges, drivers, motors, pumps, solenoids, pistons, valves, or actuators,
    wherein the other devices are mounted within the rotor, and,
    a communication mechanism that carries out communication of signals between the computer and one or more electronic devices or computers disposed in a location remote from the rotor.

9. The centrifuge of claim 1 wherein the computer is selected from the group consisting of processors, microprocessors, microcontrollers, devices with memory, devices with CPU, computers that perform communications, and computers that perform computation or decision making processes.

10. A blood processing centrifuge system, comprising:
    a rotor having an axis of rotation,
    an array of one or more blood processing stations rotating around the axis,
    whereas each station is fitted to receive fluidly interconnected containers with at least one container having blood or blood components,
    mechanical or electronics means for processing whole blood or blood components within the rotor,
    a computer controlling blood processing operations, the computer being mounted to the rotor and spinning therewith and communicating with at least a second stationary computer disposed out of the rotor,
wherein said secondary stationary computer in conjunction with the computer on the rotor control centrifuge system operations,
wherein said computer and said second stationary computer are managed by software programs that direct the blood processing operations of the blood processing centrifuge system,
the computers being selected from the group consisting of processors, microprocessors, microcontrollers, devices with memory, devices with CPU, computers that perform communications, and computers that perform computing or decision making processes, and any assembly or grouping of discrete or integrated transistors utilized in any computing or decision making process.

11. The centrifuge of claim 10 wherein the computer carries out communications between sensors, actuators, devices or controlling mechanisms located on the rotor and one or more electronic devices or computers disposed in a location remote from the rotor.

12. The centrifuge of claim 1 wherein the computer carries out communications between sensors, actuators, devices, or controlling mechanisms located on the rotor and one or more electronic devices or computers disposed in a location remote from the rotor.

13. The centrifuge of claim 10 wherein the computer includes a wireless communication mechanism, or data transmission cable mechanism connected to slip rings, the computer interconnected to the second stationary computer disposed in a location remote from the rotor.

14. The centrifuge of claim 10 wherein the second stationary computer comprises one or more of a portable computer, a stationary computer, a network of computers, a main frame, a supercomputer, a server, a remote control device, a microprocessor, video display monitor or a digital memory device.

15. The centrifuge of claim 10 wherein the computer includes:
one or more programs that include instructions for executing blood processing operations,
means for sending and receiving one or more data or instruction signals to and from other devices comprising one or more sensors, monitors, gauges, drivers, motors, pumps, solenoids, pistons, valves, or actuators,
wherein the other devices are mounted within the rotor, and
a communication mechanism that carries out communication of signals between the computer and one or more electronic devices or computers disposed in a location remote from the rotor.

16. The centrifuge of claim 10 wherein the mechanical or electronics means include one or more sensors, one or more actuators, and control mechanisms; wherein the control mechanisms comprise one or more of an electronic circuit, a pneumatic circuit, a wireless communication mechanism, a driver circuit board, a hydraulic circuit, and an electro-mechanical controller.

17. A blood processing centrifuge system, comprising:
a rotor having an axis of rotation,
mechanical or electronic means for processing whole blood or blood components within the rotor,
a computer controlling blood processing operations,
the computer being mounted to the rotor and spinning therewith,
a second stationary computer not rotating with the rotor,
the computer and the second stationary computer communicate with each other,
wherein the stationary computer in conjunction with the rotating computer control centrifuge system operations,
wherein said computer and said second stationary computer are managed by software programs that direct the blood processing operations of the blood processing centrifuge system.

18. The centrifuge of claim 17 wherein the mechanical or electronics means are selected from the group consisting of one or more sensors, one or more actuators, and one or more control mechanisms; wherein the control mechanisms are selected from the group consisting of one or more of an electronic circuit, a pneumatic circuit, a wireless communication mechanism, a driver circuit board, a hydraulic circuit, and an electro-mechanical controller.

19. The centrifuge of claim 18 wherein the one or more sensors are selected from the group consisting of a photoelectric sensor, an optic sensor, an ultrasonic sensor and a magnetic resonance imaging sensor, wherein the one or more actuators are selected from the group consisting of a valve, a pump, a motor, a solenoid, a piston, a bellow, linear driver, and electro-mechanical devices.

20. The centrifuge of claim 17 wherein the computer carries out communications between sensors, actuators, devices or controlling mechanisms located on the rotor and one or more electronic devices or computers disposed in a location remote from the rotor.

* * * * *

EX PARTE REEXAMINATION CERTIFICATE (11190th)

United States Patent
Chammas

(10) Number: US 8,876,683 C1
(45) Certificate Issued: Sep. 29, 2017

(54) AUTOMATED SYSTEM AND METHOD FOR BLOOD COMPONENTS SEPARATION AND PROCESSING

(76) Inventor: Jacques Chammas, Walpole, MA (US)

Reexamination Request:
No. 90/013,830, Oct. 7, 2016

Reexamination Certificate for:
Patent No.: 8,876,683
Issued: Nov. 4, 2014
Appl. No.: 12/139,614
Filed: Jun. 16, 2008

Related U.S. Application Data

(63) Continuation of application No. 11/076,130, filed on Mar. 9, 2005, now Pat. No. 7,442,178.

(51) Int. Cl.
*B04B 13/00* (2006.01)
*B04B 15/00* (2006.01)
*B04B 9/14* (2006.01)
*B04B 5/04* (2006.01)
*A61M 1/02* (2006.01)
*A61M 1/36* (2006.01)

(52) U.S. Cl.
CPC ............ *B04B 9/14* (2013.01); *A61M 1/0209* (2013.01); *A61M 1/3693* (2013.01); *A61M 1/3698* (2014.02); *B04B 5/0428* (2013.01); *B04B 13/00* (2013.01); *A61M 2205/331* (2013.01); *A61M 2205/3569* (2013.01); *B04B 2009/143* (2013.01)

(58) Field of Classification Search
None
See application file for complete search history.

(56) References Cited

To view the complete listing of prior art documents cited during the proceeding for Reexamination Control Number 90/013,830, please refer to the USPTO's public Patent Application Information Retrieval (PAIR) system under the Display References tab.

*Primary Examiner* — Sean E Vincent

(57) ABSTRACT

A blood processing centrifuge comprising: a rotor having an axis of rotation and being controllably spun around the axis, a mechanism for processing whole blood within the rotor while spinning, a computer controlling blood processing operations, the computer being mounted to the rotor and spinning therewith.

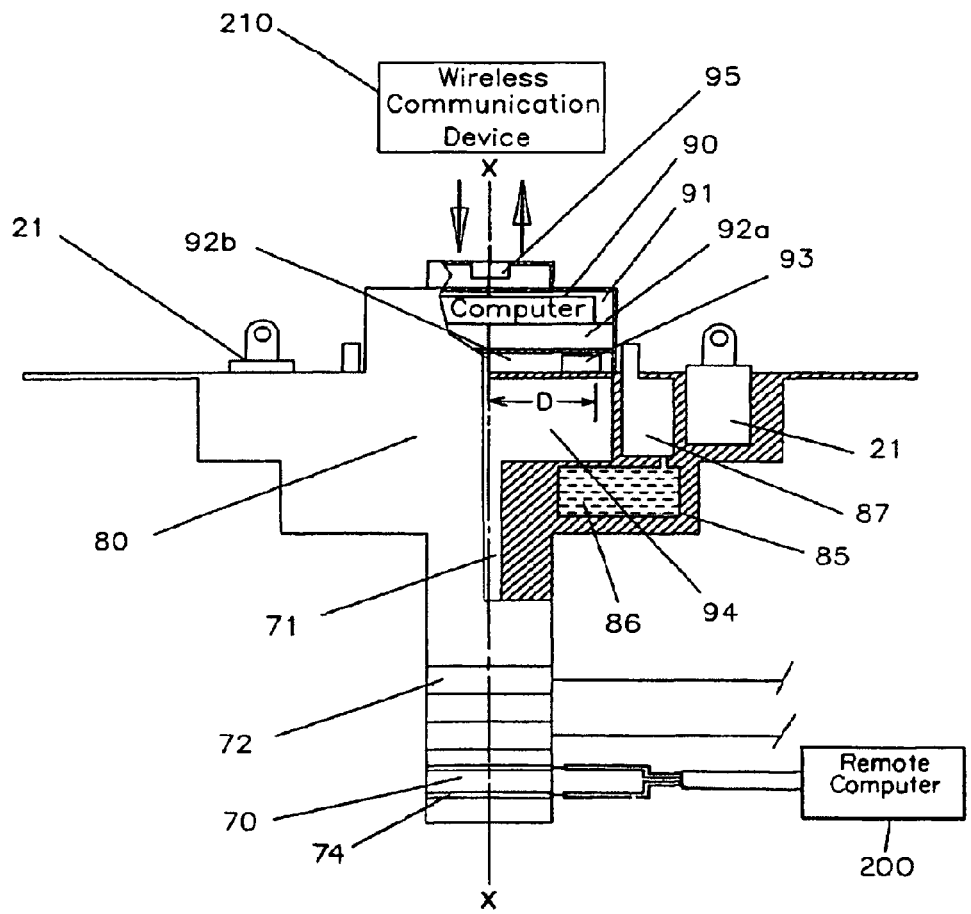

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 5, 10, 13 and 17 are determined to be patentable as amended.

Claims 2, 3, 6-9, 11, 12, 14-16 and 18-20, dependent on an amended claim, are determined to be patentable.

New claims 21-24 are added and determined to be patentable.

1. A blood processing centrifuge system, comprising:
a rotor having an axis of rotation,
mechanical or electronic means for processing whole blood or blood components within the rotor,
*at least one of a wireless transmitter and receiver or a data cable with a set of slip rings,*
a computer controlling blood processing operations the computer being mounted to the rotor and spinning therewith,
the computer mounted to and spinning with the rotor and communicating with a second stationary computer disposed in a remote location from the rotor,
*wherein, the computer mounted to the rotor is interconnected in two way communication with the second stationary computer via the at least one of the wireless transmitter and receiver or the data cable with the set of slip rings,*
wherein, the second stationary computer in conjunction with the rotating computer controls the centrifuge system operations,
wherein said computer and said second computer are managed by software programs that direct the blood processing operations of the blood processing centrifuge system.

4. The centrifuge of claim 1 wherein the computer is interconnected by *the* data [transmission wires] *cable* to the second computer disposed in a location remote from the rotor, the rotor including one or more slip rings for enabling the [wire] *data cable* interconnection.

5. The centrifuge of claim 1 wherein [the computer includes a wireless communication mechanism,] the computer *is* interconnected via the wireless [communication mechanism] *transmitter and receiver* to the second computer disposed in a location remote from the rotor.

10. A blood processing centrifuge system, comprising:
a rotor having an axis of rotation,
an array of one or more blood processing stations rotating around the axis, whereas each station is fitted to receive fluidly interconnected containers with at least one container having blood or blood components,
*at least one of a wireless transmitter and receiver or a data cable with a set of slip rings,*
mechanical or electronics means for processing whole blood or blood components within the rotor,
a computer controlling blood processing operations, the computer being mounted to the rotor and spinning therewith and communicating with at least a second stationary computer disposed out of the rotor,
wherein said secondary stationary computer in conjunction with the computer on the rotor control centrifuge system operations,
*wherein, the computer mounted to the rotor is interconnected in two way communication with the second stationary computer via the at least one of the wireless transmitter and receiver or the data cable with the set of slip rings,*
wherein said computer and said second stationary computer are managed by software programs that direct the blood processing operations of the blood processing centrifuge system, the computers being selected from the group consisting of processors, microprocessors, microcontrollers, devices with memory, devices with CPU, computers that perform communications, and computers that perform computing or decision making processes, and any assembly or grouping of discrete or integrated transistors utilized in any computing or decision making process.

13. The centrifuge of claim 10 wherein the computer includes [a] *the* wireless [communication mechanism,] *transmitter and receiver,* or *the* data [transmission] cable [mechanism] connected to *the* slip rings, the computer interconnected to the second stationary computer disposed in a location remote from the rotor.

17. A blood processing centrifuge system, comprising:
a rotor having an axis of rotation,
mechanical or electronic means for processing whole blood or blood components within the rotor,
a computer controlling blood processing operations,
*at least one of a wireless transmitter and receiver or a data cable with a set of slip rings,*
the computer being mounted to the rotor and spinning therewith,
a second stationary computer not rotating with the rotor,
the computer and the second stationary computer communicate with each other,
*wherein, the computer mounted to the rotor is interconnected in two way communication with the second stationary computer via the at least one of the wireless transmitter and receiver or the data cable with the set of slip rings,*
wherein the stationary computer in conjunction with the rotating computer control centrifuge system operations,
wherein said computer and said second stationary computer are managed by software programs that direct the blood processing operations of the blood processing centrifuge system.

*21. The centrifuge of claim 1, wherein the software programs direct blood processing operations by managing the computer mounted to the rotor to control a device or sensor located on the rotor, and receive sensor feedback,*
*the computer executing at least one of the software programs,*
*the computer mounted to the rotor sharing data with the second stationary computer.*

*22. The centrifuge of claim 1 wherein, the computer mounted to the rotor is in two way communication with the second stationary computer via the data cable with the set of slip rings.*

*23. The centrifuge in claim 1 wherein, the computer mounted to the rotor is in two way communication with the second stationary computer via the wireless transmitter and receiver.*

24. The centrifuge in claim 1 wherein, the computer mounted to the rotor is in two way communication with the second stationary computer jointly via the wireless transmitter and receiver and the data cable with the set of slip rings.

* * * * *